(12) United States Patent
Schankereli et al.

(10) Patent No.: US 12,685,630 B2
(45) Date of Patent: Jul. 21, 2026

(54) DEVICE AND SYSTEM FOR TRANSCATHETER MITRAL VALVE REPLACEMENT

(71) Applicants: COLORADO STATE UNIVERSITY RESEARCH FOUNDATION, Fort Collins, CO (US); AVALON MEDICAL, LTD., Stillwater, MN (US)

(72) Inventors: Kemal Schankereli, Stillwater, MN (US); E. Christopher Orton, Fort Collins, CO (US)

(73) Assignees: COLORADO STATE UNIVERSITY RESEARCH FOUNDATION, Fort Collins, CO (US); AVALON MEDICAL, LTD., Stillwater, MN (US)

( * ) Notice: Subject to any disclaimer, the term of this patent is extended or adjusted under 35 U.S.C. 154(b) by 838 days.

(21) Appl. No.: 17/458,745

(22) Filed: Aug. 27, 2021

(65) Prior Publication Data

US 2021/0386542 A1     Dec. 16, 2021

Related U.S. Application Data

(60) Continuation of application No. 15/163,228, filed on May 24, 2016, now Pat. No. 11,179,236, which is a
(Continued)

(51) Int. Cl.
    *A61F 2/24*          (2006.01)
    *A61F 2/95*          (2013.01)
(52) U.S. Cl.
    CPC .......... *A61F 2/2418* (2013.01); *A61F 2/2436* (2013.01); *A61F 2/2457* (2013.01);
(Continued)

(58) Field of Classification Search
    CPC .... A61F 2/2418; A61F 2/2409; A61F 2/2412; A61F 2/2454–2457
    See application file for complete search history.

(56) References Cited

U.S. PATENT DOCUMENTS

| | | | |
|---|---|---|---|
| 2,697,008 A | 12/1954 | Ross | |
| 3,409,013 A | 11/1968 | Berry | |
| | (Continued) | | |

FOREIGN PATENT DOCUMENTS

| | | |
|---|---|---|
| CN | 1486161 A | 3/2004 |
| CN | 1961845 A | 5/2007 |
| | (Continued) | |

OTHER PUBLICATIONS

US 9,155,620 B2, 10/2015, Gross et al. (withdrawn)
(Continued)

*Primary Examiner* — Shaun L David
(74) *Attorney, Agent, or Firm* — SLEMAN & LUND LLP

(57)          ABSTRACT

This invention relates to the design and function of a compressible valve replacement prosthesis which can be deployed into a beating heart without extracorporeal circulation using a transcatheter delivery system. The design as discussed focuses on the deployment of a device via a minimally invasive fashion and by way of example considers a minimally invasive surgical procedure preferably utilizing the intercostal or subxyphoid space for valve introduction. In order to accomplish this, the valve is formed in such a manner that it can be compressed to fit within a delivery system and secondarily ejected from the delivery system into the annulus of a target valve such as a mitral valve or tricuspid valve.

21 Claims, 26 Drawing Sheets

Related U.S. Application Data division of application No. 13/425,712, filed on Mar. 21, 2012, now abandoned, which is a continuation of application No. 12/963,596, filed on Dec. 8, 2010, now abandoned.

(60) Provisional application No. 61/267,739, filed on Dec. 8, 2009.

(52) U.S. Cl.
CPC ..... *A61F 2/9522* (2020.05); *A61F 2210/0014* (2013.01); *A61F 2220/0016* (2013.01); *A61F 2220/0075* (2013.01); *A61F 2230/005* (2013.01); *A61F 2230/0054* (2013.01); *A61F 2230/0078* (2013.01); *A61F 2310/00023* (2013.01)

(56) References Cited

U.S. PATENT DOCUMENTS

| | | |
|---|---|---|
| 3,472,230 A | 10/1969 | Fogarty et al. |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |

(56) References Cited

U.S. PATENT DOCUMENTS

| | | | |
|---|---|---|---|
| 6,077,214 A | 6/2000 | Mortier et al. |
| 6,099,508 A | 8/2000 | Bousquet |
| 6,132,473 A | 10/2000 | Williams et al. |
| 6,154,044 A | 11/2000 | Herr |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,371,983 B1 | 4/2002 | Lane |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |

(56) References Cited

U.S. PATENT DOCUMENTS

| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,476,101 B2 | 7/2013 | Chen |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,975,750 B2 | 5/2018 | Thomas |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0032481 A1 | 3/2002 | Gabbay |
| 2002/0116054 A1 | 8/2002 | Lundell et al. |
| 2002/0138138 A1 | 9/2002 | Yang |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0114913 A1* | 6/2003 | Spenser .................. A61F 2/243 |
|  |  | 623/2.14 |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186563 A1 | 9/2004 | Lobbi |
| 2004/0186565 A1 | 9/2004 | Schreck |
| 2004/0186566 A1 | 9/2004 | Hindrichs et al. |
| 2004/0210304 A1 | 10/2004 | Seguin et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |

(56) References Cited

U.S. PATENT DOCUMENTS

| | | |
|---|---|---|
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0149350 A1 | 7/2006 | Patel et al. |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0190074 A1 | 8/2006 | Hill et al. |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2006/0287719 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0026272 A2 | 1/2009 | Shigeta |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0125098 A1 | 5/2009 | Chuter |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |

(56) References Cited

U.S. PATENT DOCUMENTS

| | | |
|---|---|---|
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0036484 A1 | 2/2010 | Hariton et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1* | 8/2010 | Chau .................... A61F 2/2457 |
| | | 623/2.12 |
| 2010/0249489 A1 | 9/2010 | Jarvik |
| 2010/0249918 A1 | 9/2010 | Zhang |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2010/0324554 A1 | 12/2010 | Gifford |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0137410 A1 | 6/2011 | Hacohen |
| 2011/0218619 A1 | 9/2011 | Benichou et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1 | 11/2013 | Mclean |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0325114 A1 | 12/2013 | Mclean |
| 2013/0338752 A1 | 12/2013 | Geusen et al. |
| 2013/0345715 A1 | 12/2013 | Gifford |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |

(56) References Cited

U.S. PATENT DOCUMENTS

| | | |
|---|---|---|
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2018/0263618 A1 | 9/2018 | Vidlund et al. |
| 2018/0271653 A1 | 9/2018 | Vidlund et al. |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101180010 | 12/2010 |
| CN | 101984938 A | 3/2011 |
| CN | 102639179 A | 8/2012 |
| CN | 102869317 A | 1/2013 |
| CN | 102869318 A | 1/2013 |
| CN | 102869321 A | 1/2013 |
| CN | 103220993 A | 7/2013 |
| CN | 102639179 B | 10/2014 |
| DE | 1001074 B | 1/1957 |
| DE | 2246526 A1 | 3/1973 |
| DE | 2246526 B2 | 11/1980 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1264582 A2 | 12/2002 |
| EP | 1469797 | 10/2004 |
| EP | 1570809 A1 | 9/2005 |
| EP | 1469797 B1 | 11/2005 |
| EP | 1653888 A2 | 5/2006 |
| EP | 2055266 A2 | 5/2009 |
| EP | 2111800 A1 | 10/2009 |
| EP | 2193762 A1 | 6/2010 |
| EP | 2278944 A2 | 2/2011 |
| EP | 2055266 B1 | 2/2012 |
| EP | 2747707 A1 | 7/2014 |
| EP | 2918248 A1 | 9/2015 |
| FR | 2788217 A1 | 7/2000 |
| FR | 2815844 A1 | 5/2002 |
| GB | 2056023 A | 3/1981 |
| JP | 2003505146 A | 2/2003 |
| JP | 2005505343 A | 2/2005 |
| JP | 2005515836 A | 6/2005 |
| JP | 2008534085 A | 8/2008 |
| JP | 2008537891 A | 10/2008 |
| JP | 2009514628 A | 4/2009 |
| JP | 2009519783 A | 5/2009 |
| JP | 2013512765 A | 4/2013 |
| NL | 1017275 C2 | 8/2002 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 1993001768 | 2/1993 |
| WO | 9724080 A1 | 7/1997 |
| WO | 9829057 | 7/1998 |
| WO | 9933414 A1 | 7/1999 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000044313 A1 | 8/2000 |
| WO | 2000047139 A1 | 8/2000 |
| WO | 2001035878 A2 | 5/2001 |
| WO | 200149213 A2 | 7/2001 |
| WO | 0156512 A1 | 8/2001 |
| WO | 0162189 A1 | 8/2001 |
| WO | 2001054624 A1 | 8/2001 |
| WO | 2001054625 A1 | 8/2001 |
| WO | 2001061289 A1 | 8/2001 |
| WO | 0164137 A1 | 9/2001 |
| WO | 0176510 A2 | 10/2001 |
| WO | 0182840 | 11/2001 |
| WO | 2001082840 A1 | 11/2001 |
| WO | 2002004757 A1 | 1/2002 |
| WO | 0222054 A1 | 3/2002 |
| WO | 2002022054 A1 | 3/2002 |
| WO | 2002028321 A2 | 4/2002 |
| WO | 0236048 A1 | 5/2002 |
| WO | 2002041789 A2 | 5/2002 |
| WO | 0243620 A1 | 6/2002 |
| WO | 0247575 A2 | 6/2002 |
| WO | 0249540 A2 | 6/2002 |
| WO | 2002043620 A1 | 6/2002 |
| WO | 2002049540 A2 | 6/2002 |
| WO | 02076348 A1 | 10/2002 |
| WO | 2003003943 A2 | 1/2003 |
| WO | 2003003949 A2 | 1/2003 |
| WO | 2003030776 A2 | 4/2003 |
| WO | 03037227 | 5/2003 |
| WO | 03047468 A1 | 6/2003 |
| WO | 2003049619 A2 | 6/2003 |
| WO | 2004019825 A1 | 3/2004 |
| WO | 2005087140 A1 | 9/2005 |

(56)  References Cited

FOREIGN PATENT DOCUMENTS

| WO | 2005102181 A1 | 11/2005 |
| WO | 2006014233 A2 | 2/2006 |
| WO | 2006034008 A2 | 3/2006 |
| WO | 2006063199 A2 | 6/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2006135536 A2 | 12/2006 |
| WO | 2007081412 A1 | 7/2007 |
| WO | 2007100408 A2 | 9/2007 |
| WO | 2007131513 A1 | 11/2007 |
| WO | 2008005405 A2 | 1/2008 |
| WO | 2008009940 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2008150529 A1 | 12/2008 |
| WO | 2009024859 A2 | 2/2009 |
| WO | 2009026272 A1 | 2/2009 |
| WO | 2009026563 A2 | 2/2009 |
| WO | 2009033469 A1 | 3/2009 |
| WO | 2009045331 A1 | 4/2009 |
| WO | 2009045338 A1 | 4/2009 |
| WO | 2009132187 A1 | 10/2009 |
| WO | 2009134701 A2 | 11/2009 |
| WO | 2009149462 A2 | 12/2009 |
| WO | 2010090878 A2 | 8/2010 |
| WO | 2010091653 A1 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012087842 | 6/2012 |
| WO | 2012095116 A1 | 7/2012 |
| WO | 2012177942 A2 | 12/2012 |
| WO | 2013021374 A2 | 2/2013 |
| WO | 2013045262 A1 | 4/2013 |
| WO | 2013059743 | 4/2013 |
| WO | 2013059747 A1 | 4/2013 |
| WO | 2013028387 | 5/2013 |
| WO | 2013096411 A1 | 6/2013 |
| WO | 2013103612 A1 | 7/2013 |
| WO | 2013175468 A2 | 11/2013 |
| WO | 2014021905 A1 | 2/2014 |
| WO | 2014022124 A1 | 2/2014 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

Extended European Search Report including Witten Opinion for EP21155338.3 issued May 26, 2021; 7 pages.

U.S. Appl. No. 14/325,175, filed Jul. 7, 2014, Gifford Hanson.

U.S. Appl. No. 60/635,275, filed Dec. 9, 2004, Gifford Hanson.

U.S. Appl. No. 60/662,764, filed Mar. 16, 2005, Gifford Hanson.

U.S. Appl. No. 60/698,297, filed Jul. 11, 2005, Gifford Hanson.

U.S. Appl. No. 61/460,041, filed Dec. 23, 2010, Fann.

U.S. Appl. No. 61/499,630, filed Jun. 21, 2011, Gifford Hanson.

A. P. Yoganathan et al., "The Current Status of Prosthetic Heart Valves, Polymetric Materials and Artificial Organs," American Chemical Society, Mar. 20, 1983 pp. 111-150.

Al Zaibag, M. et al., "Percutaneous Balloon Valvotomy in Tricuspid Stenosis," British Heart Journal, Jan. 1987, 57 (1):51-53.

Almagor, Y. et al., "Balloon Expandable Stent Implantation in Stenotic Right Heart Valved Conduits," Journal of the American College of Cardiology, Nov. 1, 1990, 16(6):1310-1314.

Bernacca, G. M. et al., "Polyurethane heart valves: Fatigue failure, calcification, and polyurethane structure," Journal of Biomedical Materials Research, Mar. 5, 1997, 34(3):371-379.

Buckberg, G. et al., "Restoring Papillary Muscle Dimensions During Restoration in Dilated Hearts," Interactive CardioVascular and Thoracic Surgery, 2005, 4:475-477.

Choo, S. J. et al., "Aortic Root Geometry: Pattern of Differences Between Leaflets and Sinuses of Valsava," The Journal of Heart Valve Disease, Jul. 1999, 8:407-415.

Dotter, C. T. et al., "Transluminal Treatment of Arteriosclerotic Obstruction. Description of a New Technic and a Preliminary Report of its Application," Circulation, Nov. 19 6430:654-670.

Drawbaugh, K., "Feature—Heart Surgeons Explore Minimally Invasive Methods," Reuters Limited, Jul. 16, 1996, 3 pages.

International Preliminary Report on Patentability for International Application No. PCT/US2012/072282, dated Jul. 8, 2014.

International Search Report and Written Opinion for International Application No. PCT/DE2008/001515, mailed Dec. 10, 2008, 8 pages.

International Search Report and Written Opinion for International Application No. PCT/DE2009/000176, mailed Oct. 20, 2009.

International Search Report and Written Opinion for International Application No. PCT/US2010/021686, dated Sep. 3, 2010.

International Search Report and Written Opinion for International Application No. PCT/US2010/023968, mailed Oct. 19, 2010.

International Search Report and Written Opinion for International Application No. PCT/US2012/050579, mailed Feb. 28, 2013, 12 pages.

International Search Report and Written Opinion for International Application No. PCT/US2012/050740, dated Mar. 29, 2013, 10 pages.

International Search Report and Written Opinion for International Application No. PCT/US2012/072282, dated Apr. 29, 2013.

International Search Report and Written Opinion for International Application No. PCT/US2013/051308, dated Nov. 8, 2013, 13 pages.

International Search Report and Written Opinion for International Application No. PCT/US2014/040188, mailed Nov. 17, 2014.

International Search Report and Written Opinion for International Application No. PCT/US2014/044047, dated Nov. 17, 2014, 15 pages.

International Search Report and Written Opinion for International Application No. PCT/US2014/049218, dated Oct. 20, 2014, 14 pages.

International Search Report and Written Opinion for International Application No. PCT/US2014/058826, dated Jan. 20, 2015, 13 pages.

International Search Report and Written Opinion for International Application No. PCT/US2015/019418, mailed Sep. 10, 2015, 16 pages.

(56)                    References Cited

OTHER PUBLICATIONS

International Search Report and Written Opinion for PCT/IB2014/060821, mailed on Oct. 10, 2014, 12 pages.
International Search Report and Written Opinion from corresponding International Patent Application PCT/US2012/050579, dated Feb. 26, 2013.
International Search Report for International Application No. PCT/US2014/061046, mailed Feb. 24, 2015.
International Search Report for International Application No. PCT/US2006/019496, dated Dec. 18, 2006.
Invitation to Pay Additional Fees and Partial International Search Report for International Application No. PCT/US2014/040188, mailed Sep. 8, 2014, 5 pages.
Invitation to Pay Additional Fees and Partial International Search Report for International Application No. PCT/US2014/044047, mailed Sep. 8, 2014.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Liang Ma, et al., "Double-Crowned Valve Stents for Off-Pump Mitral Valve Replacement," European Journal of Cardio-Thoracic Surgery, 2005, vol. 28 pp. 194-199.
Moazami, N. et al., "Transluminal aortic valve placement: A feasibility study with a newly designed collapsible aortic valve," ASAIO Journal, Sep./ Oct. 1996 42(5):M381-M385.
Office Action for Canadian Patent Application No. 2,844,746, dated Apr. 28, 2015, 3 pages.
Rousseau, E. P. M. et al., "A mechanical analysis of the closed Hancock heart valve prosthesis," Journal of Biomechanics, 1988, 21(7):545-562.
Supplementary European Search Report for European Application No. 10738954.6, dated May 9, 2014.
Supplementary European Search Report for European Application No. 10835174.3, dated Jun. 11, 2014.
Supplementary European Search Report for European Application No. 12825480.2, dated Jul. 31, 2015.
Uchida, B. T. et al., "Modifications of Gianturco Expandable Wire Stents," Am. J. Roentgenol., May 1988, 150 (5):1185-1187.
U.S. Pat. No. 9,155,620, Oct. 2015, Gross et al. (withdrawn).
U.S. Appl. No. 13/350,310.
U.S. Appl. No. 13/356,136.
U.S. Appl. No. 14/352,964.
U.S. Appl. No. 14/352,969.
U.S. Appl. No. 61/499,632.
U.S. Appl. No. 61/549,037.
U.S. Appl. No. 61/605,699.
U.S. Appl. No. 61/760,399.
U.S. Appl. No. 61/770,986.
U.S. Appl. No. 61/825,491.
U.S. Appl. No. 61/898,345.
"Shape Memory Alloys," Retrieved from the Internet: <http://webdocs.cs.ualberta.ca/.about.database/MEMS/sma.html>, Nov. 14, 2012, 3 pages.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Boudjemline, Y. et al., "Steps Toward the Percutaneous Replacement of Atrioventricular Valves: An Experimental Study," Journal of the American College of Cardiology, Jul. 2005, 46(2):360-365.
Chamberlain, G., "Ceramics Replace Body Parts," Design News, Jun. 9, 1997, Issue 11, vol. 52, 5 pages.
Curriculum Vitae of Robert A. Ersek, M.D., FACS, Jul. 10, 2009, http://www.ersek.com/rae-cv.htm.
Decision Rejection for Japanese Patent Application No. 2012-543269, mailed Jun. 30, 2015, 5 pages.
Declaration of Malcolm J. R. Dalrymple-Hay, Nov. 9, 2012, pp. 1-11; with Curriculum Vitae, Oct. 4, 2012.
Examination Report for Application No. EP 17182203.4 dated Mar. 19, 2020, 5 pages.
Examination Report No. 1 for Australian Application No. 2015230879, dated Dec. 9, 2016, 2 pages.
Extended European Search Report for European Application No. 17182203.4, mailed Mar. 7, 2018, 9 pages.
Extended European Search Report including the Written Opinion for Application No. EP 19219651.7 dated Mar. 20, 2020, 8 pages.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142.html>, Oct. 12, 2012, 5 pages.
Gray, H., The Heart, Anatomy of the Human Body, 1918, Retrieved from the Internet <http://education.yahoo.com/reference/gray/subjects/subject/138>, Oct. 8, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.
International Search Report and Written Opinion for International Application No. PCT/US2010/059582, mailed Aug. 25, 2011, 12 pages.
Jin, X. Y. et al., "Aortic Root Geometry and Stentless Porcine Valve Competence," Seminars in Thoracic and Cardiovascular Surgery, Oct. 1999, 11(4):145-150.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Notice of Reasons for Rejection for Japanese Patent Application No. 2015-216031, dated Oct. 18, 2016, 13 pages.
Office Action for Australian Patent Application No. 2010328106, dated Jan. 2, 2014, 4 pages.
Office Action for Australian Patent Application No. 2010328106, dated Jun. 4, 2015, 4 pages.
Office Action for Australian Patent Application No. 2010328106, dated Sep. 8, 2015, 3 pages.
Office Action for Canadian Application No. 2,783,282, dated Sep. 29, 2016, 3 pages.
Office Action for Japanese Patent Application No. 2012-543269, mailed Sep. 9, 2014, 8 pages.

(56) References Cited

OTHER PUBLICATIONS

Office Action for U.S. Appl. No. 12/963,596, mailed Jul. 17, 2013, 32 pages.
Office Action for U.S. Appl. No. 12/963,596, mailed Jul. 29, 2014, 23 pages.
Office Action for U.S. Appl. No. 13/425,712, mailed Apr. 22, 2014, 14 pages.
Office Action for U.S. Appl. No. 13/425,712, mailed Aug. 16, 2013, 14 pages.
Office Action for U.S. Appl. No. 13/425,712, mailed Feb. 24, 2016, 11 pages.
Office Action for U.S. Appl. No. 13/425,712, mailed Jun. 18, 2015, 13 pages.
Orton, C., "Mitralseal: Hybrid Transcatheter Mitral Valve Replacement," Symposium: Small Animal Proceedings, 2011, pp. 311-312.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.
Robert C. Ashton Jr., "Development of an Intraluminal Device for the Treatment of Aortic Regurgitation: Prototype and In Vitro Testing System," Journal of Thoracic and Cardiovascular Surgery, 1996, Issue/vol. 112, pp. 979-983.
Rosch, J. et al., "The Birth, Early Years and Future of Interventional Radiology," J Vasc Interv Radiol., Jul. 2003, 4:841-853.

Ross, D. N., "Aortic Valve Surgery," Guy's Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Supplementary Search Report for European Application No. 10836657. 6, mailed Jan. 5, 2015, 6 pages.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
Urban, P., "Coronary Artery Stenting," Editions Medecine et Hygiene, Genève, 1991, pp. 5-47.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.

* cited by examiner

124

122

112

114

128

120

148

126

146

110

134

116

110

134

DEVICE AND SYSTEM FOR TRANSCATHETER MITRAL VALVE REPLACEMENT

CROSS REFERENCE TO RELATED APPLICATIONS

This application is a continuation of U.S. patent application Ser. No. 15/163,228, filed May 24, 2016, which is a divisional of U.S. patent application Ser. No. 13/425,712, filed Mar. 31, 2012, which is a continuation of U.S. patent application Ser. No. 12/963,596, filed Dec. 8, 2010, which claims priority to U.S. Provisional Application Ser. No. 61/267,739, filed Dec. 8, 2009, each of the disclosures of which is incorporated herein by reference in its entirety.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

This invention relates to a transcatheter mitral valve replacement and a delivery system therefor.

Background of the Invention

The current state of knowledge is as follows.

Valvular heart disease and specifically aortic and mitral valve disease is a significant health issue in the US. Annually approximately 90,000 valve replacements are conducted in the US. Traditional valve replacement surgery, the orthotopic replacement of a heart valve, is an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients.

Thus if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated to the native mitral valve apparatus and thus a greater level of difficulty with regards to inserting and anchoring the replacement prosthesis.

Several designs for catheter-deployed (transcatheter) aortic valve replacement are under various stages of development. The Edwards SAPIEN transcatheter heart valve is currently undergoing clinical trial in patients with calcific aortic valve disease who are considered high-risk for conventional open-heart valve surgery. This valve is deployable via a retrograde transarterial (transfemoral) approach or an antegrade transapical (transventricular) approach. A key aspect of the Edwards SAPIEN and other transcatheter aortic valve replacement designs is their dependence on lateral fixation (e.g. tines) that engages the valve tissues as the primary anchoring mechanism. Such a design basically relies on circumferential friction around the valve housing or stent to prevent dislodgement during the cardiac cycle. This anchoring mechanism is facilitated by, and may somewhat depend on, a calcified aortic valve annulus. This design also requires that the valve housing or stent have a certain degree of rigidity.

At least one transcatheter mitral valve design is currently in development. The Endovalve uses a folding tripod-like design that delivers a tri-leaflet bioprosthetic valve. It is designed to be deployed from a minimally invasive transatrial approach, and could eventually be adapted to a transvenous atrial septostomy delivery. This design uses "proprietary gripping features" designed to engage the valve annulus and leaflets tissues. Thus the anchoring mechanism of this device is essentially equivalent to that used by transcatheter aortic valve replacement designs.

BRIEF SUMMARY OF THE INVENTION

The present invention relates to the design and function of a compressible prosthetic heart valve replacement which can be deployed into a closed beating heart using a transcatheter delivery system. The design as discussed focuses on the deployment of a device via a minimally invasive fashion and by way of example considers a minimally invasive surgical procedure utilizing the intercostal or subxyphoid space for valve introduction. In order to accomplish this, the valve is formed in such a manner that it can be compressed to fit within a delivery system and secondarily ejected from the delivery system into the target location, for example the mitral or tricuspid valve annulus.

In a preferred embodiment, there is provided a prosthetic mitral valve containing a cuff which locally contours to the mitral annulus.

In another preferred embodiment, there is provided a prosthetic heart valve with a cuff that has a tissue or synthetic covering.

In another preferred embodiment, there is provided a prosthetic heart valve with a cuff that has articulating wire loops of various lengths.

In another preferred embodiment, there is provided a prosthetic heart valve containing at least one elastic tether to provide compliance during the physiologic movement or conformational changes associated with heart contraction.

In another preferred embodiment, there is provided a prosthetic heart valve having a stent body and cuff that are made from a superelastic metal.

In another preferred embodiment, there is provided a prosthetic heart valve having a stent body and cuff that are made from a superelastic metal that is laser cut with predetermined shapes to facilitate collapsing into the catheter delivery system.

In another preferred embodiment, there is provided a prosthetic heart valve having a stent body constructed from ductile metal, for example stainless steel, so as to require a balloon for expansion once located at the annulus, but capable of deformation without fracture.

In another preferred embodiment, there is provided a prosthetic heart valve constructed from superelastic wire made from a shape memory alloy such as nickel-titanium alloy (Naval Ordinance Lab) Nitinol™.

In another preferred embodiment, there is provided a laser cut prosthetic heart valve containing tethers for anchoring.

In another preferred embodiment, there is provided a valve constructed from wire containing tethers for anchoring.

In another preferred embodiment, there is provided a valve containing tether which are used to position the valve cuff into the mitral annulus to prevent perivalvular leak.

In another preferred embodiment, there are tethers that are bioabsorbable and provide temporary anchoring until biological fixation of the prosthesis occurs. Biological fixation consisting of fibrous adhesions between the leaflet tissues and prosthesis or compression on the prosthesis by reversal of heart dilation, or both.

In another preferred embodiment, there is provided a prosthetic heart valve constructed from wire or laser-formed demonstrating a compliant body and cuff such that the two components accommodate the movement of the heart throughout the cardiac cycle.

In another preferred embodiment, there is provided a cuff for a prosthetic heart valve, said cuff being covered with tissue.

In another preferred embodiment, there is provided a cuff for a prosthetic heart valve, said cuff being covered with a synthetic polymer selected from expandable poly-tetrafluoroethylene (ePTFE) or polyester.

In another preferred embodiment, there is provided a prosthetic heart valve that has leaflet material constructed from a material selected from the group consisting of polyurethane, polytetrafluoroethylene, pericardium, and small intestine submucosa.

In another preferred embodiment, there is provided a prosthetic heart valve having surfaces that are treated with anticoagulant.

In another preferred embodiment, there is provided a prosthetic heart valve having a cuff and containing anchoring tethers which are attached to the cuff.

In another preferred embodiment, there is provided a prosthetic heart valve having a cuff and containing anchoring tethers which are attached to the cuff and at both commissural tips.

In another preferred embodiment, there is provided a prosthetic heart valve having a cuff where the cuff attachment relative to the body is within the angles of about 60 degrees to about 150 degrees.

In another preferred embodiment, there is provided a prosthetic heart valve containing a combination of tethers and barbs useful for anchoring the device into the mitral annulus.

In a preferred embodiment, there is provided a prosthetic heart valve which comprises an expandable tubular stent having a cuff and an expandable internal leaflet assembly, said leaflet assembly may or may not have a structural wire support, wherein said cuff is comprised of wire covered with stabilized tissue, and wherein said leaflet assembly is disposed within the stent and is comprised of stabilized tissue in the form of leaflets.

In another embodiment, there is provided a feature wherein the wire of the cuff is formed as a series of radially extending loops of equal or variable length.

In another embodiment, there is provided a feature wherein the cuff extends laterally beyond the expanded tubular stent according to a ratio of the relationship between the height of the expanded deployed stent (h) and the lateral distance that the cuff extends onto the tissue (l). Preferably, the h/l ratio can range from 1:10 to 10:1, and more preferably includes without limitation 1:3, 1:2, 1:1, 2:1, and fractional ranges there between such as 1.25:2.0, 1.5:2.0, and so forth. It is contemplated in one non-limiting example that the cuff can extend laterally (1) between about 3 and about 30 millimeters.

In another embodiment, there is provided a feature wherein the tubular stent has a first end and a second end, wherein the cuff is formed from the stent itself, or in the alternative is formed separately and wherein the cuff is located at the first end of the stent, and the second end of the tubular stent has a plurality of tether attachment structures.

In another embodiment, there is provided a feature further comprising a plurality of tethers for anchoring the prosthetic heart valve to tissue and/or for positioning the prosthetic heart valve.

In another embodiment, there is provided a feature further comprising an epicardial tether securing device, wherein the tethers extend between about 3 and about 8 cm in length, and are fastened to an epicardial tether securing device.

In another embodiment, there is provided a catheter delivery system for delivery of a prosthetic heart valve which comprises a delivery catheter having the prosthetic heart valve disposed therein, and an obturator for expelling the prosthetic heart valve.

In another embodiment, there is provided an assembly kit for preparing the catheter delivery system which comprises a compression funnel, an introducer, a wire snare, an obturator, a delivery catheter, and a prosthetic heart valve, wherein the compression funnel has an aperture for attaching to the introducer, wherein said introducer is comprised of a tube having a diameter that fits within the diameter of the delivery catheter, wherein said obturator is comprised of a tube fitted with a handle at one end and a cap at the other end, wherein here said cap has an opening to allow the wire snare to travel therethrough, and said obturator has a diameter that fits within the diameter of the introducer, and wherein said prosthetic heart valve is compressible and fits within the delivery catheter.

In another embodiment, there is provided a method of treating mitral regurgitation and/or tricuspid regurgitation in a patient, which comprises the step of surgically deploying the prosthetic heart valve into the annulus of the target valve structure, e.g. mitral valve annulus and tricuspid valve annulus of the patient.

In another embodiment, there is provided a feature wherein the prosthetic heart valve is deployed by directly accessing the heart through an intercostal space, using an apical approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through a thoracotomy, sternotomy, or minimally-invasive thoracic, thorascopic, or transdiaphragmatic approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through the intercostal space, using a lateral approach to enter the left or right ventricle, and deploying the prosthetic heart valve into the valvular annulus using the catheter delivery system.

In another embodiment, there is provided a feature wherein the prosthetic heart valve is deployed by accessing the left heart using either an antegrade-trans(atrial)septal (transvenous-trans(atrial)septal) approach or a retrograde (transarterial-transaortic) catheter approach to enter the left heart, and deploying the prosthetic heart valve into the mitral annulus using the catheter delivery system.

In another embodiment, there is provided a feature wherein the prosthetic heart valve is deployed into the mitral annulus from a retrograde approach by accessing the left ventricle through the apex of the ventricular septum (transvenous-trans(ventricular)septal approach).

In another embodiment, there is a feature wherein the prosthetic heart valve is deployed into the mitral position using a retrograde transventricular septal approach and the tethers are anchored into or on the right ventricular side of the ventricular septum.

In another embodiment, there is provided a feature further comprising tethering the prosthetic heart valve to tissue within the left ventricle.

In another embodiment, there is provided a feature wherein the prosthetic heart valve is tethered to the apex of the left ventricle using an epicardial tether securing device. In another embodiment, such device is fashioned as a pledget, button or similar article.

In another embodiment, there is provided a retrieval method for quickly removing a prosthetic heart valve having one or more tethers from a patient using minimally invasive cardiac catheter techniques, which comprises the steps of, capturing the one or more tethers with a catheter having a snare attachment, guiding the captured tethers into a collapsible funnel attachment connected to the removal catheter, pulling the tethers to conform the prosthetic heart valve into a collapsed, compressed conformation, and pulling the now compressed prosthetic heart valve into the removal catheter for subsequent extraction. The retrieval method is contemplated for use for capturing the prosthetic heart valve as described herein or any suitable tethered, collapsible medical device. In a preferred embodiment, the method is used to extract a prosthetic heart valve from either the left or right ventricle. The method may be particularly useful to extract the prosthetic appliance during an aborted surgical deployment.

BRIEF DESCRIPTION OF THE DRAWINGS

FIG. 5 shows the tethers without the structural wire support for the leaflets.

FIG. 17 shows the delivery catheter advanced to through the mitral valve and into the left atrium for deployment of the prosthetic valve.

FIG. 21 A is a detailed drawing of the flexible delivery catheter inserted into the left ventricular apex along with four sutures having partially installed apical-closure/tissue-buttressing material. FIG. 21 B is a detailed drawing of the anchoring system of the prosthetic valve in which the ventricular tethers are shown treaded through the left ventricle apex and through a partially installed pledget; also shown are fully installed apical-closure material.

FIG. 23 shows the delivery catheter advanced through to the tricuspid valve and into the right atrium for deployment of the prosthetic valve.

FIG. 24 B is a top view from slightly above the horizontal plane of one embodiment of a prosthetic valve according to the present invention to show the top surface of the cuff.

DETAILED DESCRIPTION OF THE INVENTION

Figure 1:
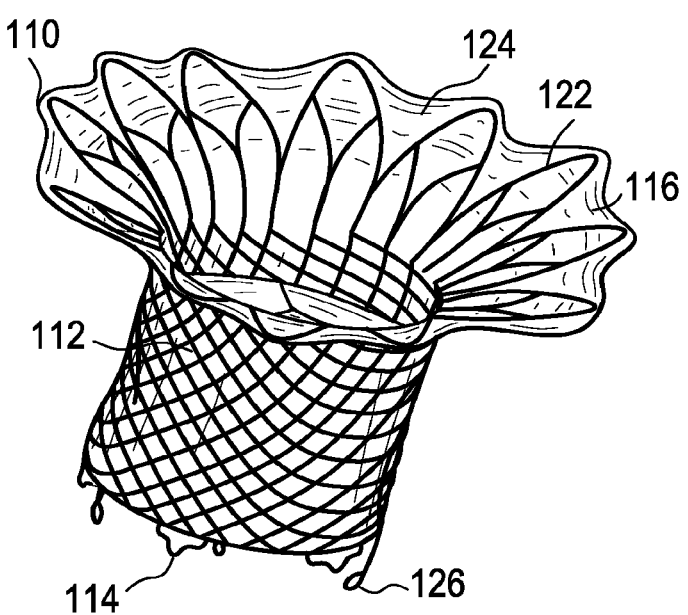
FIG. 1 is a perspective view of one embodiment of a prosthetic valve according to the present invention.

The present invention provides in one embodiment a prosthetic heart valve that comprises a self-expanding valve assembly that is anchored within the mitral valve of the heart using an integral cuff to anchor the valve and using one or more tethers anchored to the heart. It is contemplated as within the scope of the invention to provide a prosthetic heart valve having as an anchoring system both an integral cuff or collar and one or more tethers for tissue anchoring.

The prosthetic heart valve comprises a self-expanding tubular stent having a cuff at one end and tether loops for attaching tethers at the other end, and disposed within the tubular stent is a leaflet assembly that contains the valve leaflets, the valve leaflets being formed from stabilized tissue or other suitable biological or synthetic material. In one embodiment, the leaflet assembly comprises a wire form where a formed wire structure is used in conjunction with stabilized tissue to create a leaflet support structure which can have anywhere from 1, 2, 3 or 4 leaflets, or valve cusps disposed therein. In another embodiment, the leaflet assembly is wireless and uses only the stabilized tissue and stent body to provide the leaflet support structure, without using wire, and which can also have anywhere from 1, 2, 3 or 4 leaflets, or valve cusps disposed therein.

Functions of the Cuff

The cuff functions in a variety of ways. The first function of the cuff is to inhibit perivalvular leak/regurgitation of blood around the prosthesis. By flexing and sealing across the irregular contours of the annulus and atrium, leaking is minimized and/or prevented.

The second function of the cuff is to provide an adjustable and/or compliant bio-prosthetic valve. The heart and its structures undergo complex conformational changes during the cardiac cycle. For example, the mitral valve annulus has a complex geometric shape known as a hyperbolic paraboloid much like a saddle, with the horn being anterior, the seat back being posterior, and the left and right valleys located medially and laterally. Beyond this complexity, the area of the mitral annulus changes over the course of the cardiac cycle. Further, the geometry of the tricuspid valve and tricuspid annulus continues to be a topic of research, posing its own particular problems. Accordingly, compliance is a very important but unfortunately often overlooked requirement of cardiac devices. Compliance here refers to the ability of the valve to maintain structural position and integrity during the cardiac cycle. Compliance with the motion of the heart is a particularly important feature, especially the ability to provide localized compliance where the underlying surfaces are acting differently from the adjacent surfaces. This ability to vary throughout the cardiac cycle allows the valve to remain seated and properly deployed in a manner not heretofore provided.

Additionally, compliance may be achieved through the use of the tethers where the tethers are preferably made from an elastic material. Tether-based compliance may be used alone, or in combination with the cuff-based compliance.

The third function of the cuff valve is to provide a valve that, during surgery, is able to be seated and be able to contour to the irregular surfaces of the atrium. The use of independent tethers allows for side to side fitting of the valve within the annulus. For example, where three tethers are used, they are located circumferentially about 120 degrees relative to each other which allows the surgeon to observe whether or where perivalvular leaking might be occurring and to pull on one side or the other to create localized pressure and reduce or eliminate the leaking.

The fourth function of the cuff is to counter the forces that act to displace the prosthesis toward/into the ventricle (i.e. atrial pressure and flow-generated shear stress) during ventricular filling.

Additional features of the cuff include that it functions to strengthen the leaflet assembly/stent combination by providing additional structure. Further, during deployment, the cuff functions to guide the entire structure, the prosthetic valve, into place at the mitral annulus during deployment and to keep the valve in place once it is deployed.

Cuff Structure

The cuff is a substantially flat plate that projects beyond the diameter of the tubular stent to form a rim or border. As used herein, the term cuff, flange, collar, bonnet, apron, or skirting are considered to be functionally equivalent. When the tubular stent is pulled through the mitral valve aperture, the mitral annulus, by the tether loops in the direction of the left ventricle, the cuff acts as a collar to stop the tubular stent from traveling any further through the mitral valve aperture. The entire prosthetic valve is held by longitudinal forces between the cuff which is seated in the left atrium and mitral annulus, and the ventricular tethers attached to the left ventricle.

The cuff is formed from a stiff, flexible shape-memory material such as the nickel-titanium alloy material Nitinol™ wire that is covered by stabilized tissue or other suitable biocompatible or synthetic material. In one embodiment, the cuff wire form is constructed from independent loops of wire that create lobes or segments extending axially around the circumference of the bend or seam where the cuff transitions to the tubular stent (in an integral cuff) or where the cuff is attached to the stent (where they are separate, but joined components).

Once covered by stabilized tissue or material, the loops provide the cuff the ability to travel up and down, to articulate, along the longitudinal axis that runs through the center of the tubular stent. In other words, the individual spindles or loops can independently move up and down, and can spring back to their original position due to the relative stiffness of the wire. The tissue or material that covers the cuff wire has a certain modulus of elasticity such that, when attached to the wire of the cuff, is able to allow the wire spindles to move. This flexibility gives the cuff, upon being deployed within a patient's heart, the ability to conform to the anatomical shape necessary for a particular application. In the example of a prosthetic mitral valve, the cuff is able to conform to the irregularities of the left atrium and shape of the mitral annulus, and to provide a tight seal against the atrial tissue adjacent the mitral annulus and the tissue within the mitral annulus. As stated previously, this feature importantly provides a degree of flexibility in sizing a mitral valve and prevents blood from leaking around the implanted prosthetic heart valve.

An additional important aspect of the cuff dimension and shape is that, when fully seated and secured, the edge of the cuff preferably should not be oriented laterally into the atrial wall such that it can produce a penetrating or cutting action on the atrial wall.

In one preferred embodiment, the wire spindles of the cuff are substantially uniform in shape and size. In another preferred embodiment of the present invention, each loop or spindle may be of varying shapes and sizes. In this example, it is contemplated that the loops may form a pattern of alternating large and small loops, depending on where the valve is being deployed. In the case of a prosthetic mitral valve, pre-operative imaging may allow for customizing the structure of the cuff depending on a particular patient's anatomical geometry in the vicinity of the mitral annulus.

The cuff wire form is constructed so as to provide sufficient structural integrity to withstand the intracardiac forces without collapsing. The cuff wire form is preferably constructed of a superelastic metal, such as Nitinol™® and is capable of maintaining its function as a scaling collar for the tubular stent while under longitudinal forces that might cause a structural deformation or valve displacement. It is contemplated as within the scope of the invention to optionally use other shape memory alloys such as Cu—Zn—Al—Ni alloys, and Cu—Al—Ni alloys. The heart is known to generate an average left atrial pressure between about 8 and 30 mm Hg (about 0.15 to 0.6 psi). This left atrial filling pressure is the expected approximate pressure that would be exerted in the direction of the left ventricle when the prosthesis is open against the outer face of the cuff as an anchoring force holding the cuff against the atrial tissue that is adjacent the mitral valve. The cuff counteracts this longitudinal pressure against the prosthesis in the direction of the left ventricle to keep the valve from being displaced or slipping into the ventricle. In contrast, left ventricular systolic pressure, normally about 120 mm Hg, exerts a force on the closed prosthesis in the direction of the left atrium. The tethers counteract this force and are used to maintain the valve position and withstand the ventricular force during ventricular contraction or systole. Accordingly, the cuff has sufficient structural integrity to provide the necessary tension against the tethers without being dislodged and pulled into the left ventricle. After a period of time, changes in the geometry of the heart and/or fibrous adhesion between prosthesis and surrounding cardiac tissues may assist or replace the function of the ventricular tethers in resisting longitudinal forces on the valve prosthesis during ventricular contraction.

Stent Structure

Preferably, superelastic metal wire, such as Nitinol™ wire, is used for the stent, for the inner wire-based leaflet assembly that is disposed within the stent, and for the cuffwire form. As stated, it is contemplated as within the scope of the invention to optionally use other shape memory alloys such as Cu—Zn—Al—Ni alloys, and Cu—Al—Ni alloys. It is contemplated that the stent may be constructed as a braided stent or as a laser cut stent. Such stents are available from any number of commercial manufacturers, such as Pulse Systems. Laser cut stents are preferably made from Nickel-Titanium (Nitinol™), but also without limitation made from stainless steel, cobalt chromium, titanium, and other functionally equivalent metals and alloys, or Pulse Systems braided stent that is shape-set by heat treating on a fixture or mandrel.

One key aspect of the stent design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required compression features.

Laser Cut Stent

One possible construction of the stent envisions the laser cutting of a thin, isodiametric Nitinol tube. The laser cuts form regular cutouts in the thin Nitinol tube. Secondarily the tube is placed on a mold of the desired shape, heated to the Martensitic temperature and quenched. The treatment of the stent in this manner will form a stent or stent/cuff that has shape memory properties and will readily revert to the memory shape at the calibrated temperature.

Braided Wire Stent

A stent can be constructed utilizing simple braiding techniques. Using a Nitinol wire for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided stent is placed on a shaping fixture and placed in a muffle furnace at a specified temperature to set the stent to the desired shape and to develop the martensitic or super elastic properties desired.

The stent as envisioned in one preferred embodiment is designed such that the ventricular aspect of the stent comes to 2-5 points onto which anchoring sutures are affixed. The anchoring sutures (tethers) will traverse the ventricle and ultimately be anchored to the epicardial surface of the heart approximately at the level of the apex. The tethers when installed under slight tension will serve to hold the valve in place, i.e. inhibit paravalvular leakage during systole.

Leaflet and Assembly Structure

The valve leaflets are held by, or within, a leaflet assembly. In one preferred embodiment of the invention, the leaflet assembly comprises a leaflet wire support structure to which the leaflets are attached and the entire leaflet assembly is housed within the stent body. In this embodiment, the assembly is constructed of wire and stabilized tissue to form a suitable platform for attaching the leaflets. In this aspect, the wire and stabilized tissue allow for the leaflet structure to be compressed when the prosthetic valve is compressed within the deployment catheter, and to spring open into the proper functional shape when the prosthetic valve is opened during deployment. In this embodiment, the leaflet assembly may optionally be attached to and housed within a separate cylindrical liner made of stabilized tissue or material, and the liner is then attached to line the interior of the stent body.

In this embodiment, the leaflet wire support structure is constructed to have a collapsible/expandable geometry. In a preferred embodiment, the structure is a single piece of wire. The wire form is, in one embodiment, constructed from a shape memory alloy such as Nitinol. The structure may optionally be made of a plurality of wires, including between 2 to 10 wires. Further, the geometry of the wire form is without limitation, and may optionally be a series of parabolic inverted collapsible arches to mimic the saddle-like shape of the native annulus when the leaflets are attached. Alternatively, it may optionally be constructed as collapsible concentric rings, or other similar geometric forms that are able to collapse/compress which is followed by an expansion to its functional shape. In certain preferred embodiments, there may be 2, 3 or 4 arches. In another embodiment, closed circular or ellipsoid structure designs are contemplated. In another embodiment, the wire form may be an umbrella-type structure, or other similar unfold-and-lock-open designs. A preferred embodiment utilizes super elastic Nitinol wire approximately 0.015" in diameter. In this embodiment, the wire is wound around a shaping fixture in such a manner that 2-3 commissural posts are formed. The fixture containing the wrapped wire is placed in a muffle furnace at a pre-determined temperature to set the shape of the wire form and to impart its super elastic properties. Secondarily, the loose ends of the wire form are joined with a stainless steel or Nitinol tube and crimped to form a continuous shape. In another preferred embodiment, the commissural posts of the wire-form are adjoined at their tips by a circular connecting ring, or halo, whose purpose is to minimize inward deflection of the post(s).

In another preferred embodiment, the leaflet assembly is constructed solely of stabilized tissue or other suitable material without a separate wire support structure. The leaflet assembly in this embodiment is also disposed within the lumen of the stent and is attached to the stent to provide a sealed joint between the leaflet assembly and the inner wall of the stent. By definition, it is contemplated within the scope of the invention that any structure made from stabilized tissue and/or wire(s) related to supporting the leaflets within the stent constitute a leaflet assembly. In this embodiment, stabilized tissue or suitable material may also optionally be used as a liner for the inner wall of the stent and is considered part of the leaflet assembly.

Liner tissue or biocompatible material may be processed to have the same or different mechanical qualities, e.g. thickness, durability, etc. from the leaflet tissue.

Deployment within the Valvular Annulus

The prosthetic heart valve is, in one embodiment, apically delivered through the apex of the left ventricle of the heart using a catheter system. In one aspect of the apical delivery, the catheter system accesses the heart and pericardial space by intercostal delivery. In another delivery approach, the catheter system delivers the prosthetic heart valve using either an antegrade or retrograde delivery approach using a flexible catheter system, and without requiring the rigid tube system commonly used. In another embodiment, the catheter system accesses the heart via a trans-septal approach.

In one non-limiting preferred embodiment, the stent body extends into the ventricle about to the edge of the open mitral valve leaflets (approximately 25% of the distance between the annulus and the ventricular apex). The open native leaflets lay against the outside stent wall and parallel to the long axis of the stent (i.e. the stent holds the native mitral valve open).

In one non-limiting preferred embodiment, the diameter should approximately match the diameter of the mitral annulus. Optionally, the valve may be positioned to sit in the mitral annulus at a slight angle directed away from the aortic valve such that it is not obstructing flow through the aortic valve. Optionally, the outflow portion (bottom) of the stent should not be too close to the lateral wall of the ventricle or papillary muscle as this position may interfere with flow through the prosthesis. As these options relate to the tricuspid, the position of the tricuspid valve may be very similar to that of the mitral valve.

In another embodiment, the prosthetic valve is sized and configured for use in areas other than the mitral annulus, including, without limitation, the tricuspid valve between the right atrium and right ventricle. Alternative embodiments may optionally include variations to the cuff structure to accommodate deployment to the pulmonary valve between the right ventricle and pulmonary artery, and the aortic valve between the left ventricle and the aorta. In one embodiment, the prosthetic valve is optionally used as a venous backflow valve for the venous system, including without limitation the vena cava, femoral, subclavian, pulmonary, hepatic, renal and cardiac. In this aspect, the cuff feature is utilized to provide additional protection against leaking.

Tethers

In one preferred embodiment, there are tethers attached to the prosthetic heart valve that extend to one or more tissue anchor locations within the heart. In one preferred embodiment, the tethers extend downward through the left ventricle, exiting the left ventricle at the apex of the heart to be fastened on the epicardial surface outside of the heart. Similar anchoring is contemplated herein as it regards the tricuspid, or other valve structure requiring a prosthetic. There may be from 2 to 8 tethers which are preferably attached to the stent.

In another preferred embodiment, the tethers may optionally be attached to the cuff to provide additional control over position, adjustment, and compliance. In this preferred embodiment, one or more tethers are optionally attached to the cuff, in addition to, or optionally, in place of, the tethers attached to the stent. By attaching to the cuff and/or the stent, an even higher degree of control over positioning, adjustment, and compliance is provided to the operator during deployment.

During deployment, the operator is able to adjust or customize the tethers to the correct length for a particular patient's anatomy. The tethers also allow the operator to tighten the cuff onto the tissue around the valvular annulus by pulling the tethers, which creates a leak-free seal.

In another preferred embodiment, the tethers are optionally anchored to other tissue locations depending on the particular application of the prosthetic heart valve. In the case of a mitral valve, or the tricuspid valve, there are optionally one or more tethers anchored to one or both papillary muscles, septum, and/or ventricular wall.

The tethers, in conjunction with the cuff, provide for a compliant valve which has heretofore not been available.

The tethers are made from surgical-grade materials such as biocompatible polymer suture material. Examples of such material include 2-0 exPTFE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle. Upon being drawn to and through the apex of the heart, the tethers may be fastened by a suitable mechanism such as tying off to a pledget or similar adjustable button-type anchoring device to inhibit retraction of the tether back into the ventricle. It is also contemplated that the tethers might be bioresorbable/bioabsorbable and thereby provide temporary fixation until other types of fixation take hold such a biological fibrous adhesion between the tissues and prosthesis and/or radial compression from a reduction in the degree of heart chamber dilation.

Further, it is contemplated that the prosthetic heart valve may optionally be deployed with a combination of installation tethers and permanent tethers, attached to either the stent or cuff, or both, the installation tethers being removed after the valve is successfully deployed. It is also contemplated that combinations of inelastic and elastic tethers may optionally be used for deployment and to provide structural and positional compliance of the valve during the cardiac cycle.

Pledget

In one embodiment, to control the potential tearing of tissue at the apical entry point of the delivery system, a circular, semi-circular, or multi-part pledget is employed. The pledget may be constructed from a semi-rigid material such as PFTE felt. Prior to puncturing of the apex by the delivery system, the felt is firmly attached to the heart such that the apex is centrally located. Secondarily, the delivery system is introduced through the central area, or orifice as it may be, of the pledget. Positioned and attached in this manner, the pledget acts to control any potential tearing at the apex.

Tines/Barbs

In another embodiment the valve can be seated within the valvular annulus through the use of tines or barbs. These may be used in conjunction with, or in place of one or more tethers. The tines or barbs are located to provide attachment to adjacent tissue. In one preferred embodiment, the tines are optionally circumferentially located around the bend/transition area between the stent and the cuff. Such tines are forced into the annular tissue by mechanical means such as using a balloon catheter. In one non-limiting embodiment, the tines may optionally be semi-circular hooks that upon expansion of the stent body, pierce, rotate into, and hold annular tissue securely.

Stabilized Tissue or Biocompatible Material

In one embodiment, it is contemplated that multiple types of tissue and biocompatible material may be used to cover the cuff, to form the valve leaflets, to form a wireless leaflet assembly, and/or to line both the inner and/or outer lateral walls of the stent. As stated previously, the leaflet component may be constructed solely from stabilized tissue, without using wire, to create a leaflet assembly and valve leaflets. In this aspect, the tissue-only leaflet component may be attached to the stent with or without the use of the wire form. In a preferred embodiment, there can be anywhere from 1, 2, 3 or 4 leaflets, or valve cusps.

It is contemplated that the tissue may be used to cover the inside of the stent body, the outside of the stent body, and the top and/or bottom side of the cuff wire form, or any combination thereof.

In one preferred embodiment, the tissue used herein is optionally a biological tissue and may be a chemically stabilized valve of an animal, such as a pig. In another preferred embodiment, the biological tissue is used to make leaflets that are sewn or attached to a metal frame. This tissue is chemically stabilized pericardial tissue of an animal, such as a cow (bovine pericardium) or sheep (ovine pericardium) or pig (porcine pericardium) or horse (equine pericardium).

Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses a cellular collagen-based tissue matrix for transplantation.

In one preferred embodiment, the valve leaflets may optionally be made from a synthetic material such as a polyurethane or polytetrafluoroethylene. Where a thin, durable synthetic material is contemplated, e.g. for covering the cuff, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, siliconepolycarbonate urethane, and ultra-high molecular weight polyethylene. Additional biocompatible polymers may optionally include polyolefins, elastomers, polyethyleneglycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

In another embodiment, the valve leaflets may optionally have a surface that has been treated with (or reacted with) an anti-coagulant, such as, without limitation, immobilized heparin. Such currently available heparinized polymers are known and available to a person of ordinary skill in the art.

Alternatively, the valve leaflets may optionally be made from pericardial tissue or small intestine submucosal tissue.

Manufacture of Ultra-Thin Stabilized Tissue

In a preferred embodiment, ultra-thin vapor-cross linked stabilized bioprosthetic or implant tissue material is contemplated. Tissue having a 0.003' (0.0762 mm) to about 0.010" (0.254 mm) may be made using a process comprising the steps of: (a) vapor cross-linking a pre-digested compressed tissue specimen by exposing the tissue specimen to a vapor of a cross-linking agent selected from the group consisting of aldehydes, epoxides, isocyanates, carbodiimides, isothiocyanates, glycidalethers, and acyl azides; and (b) chemically cross-linking the vapor-cross-linked tissue specimen by exposing the vapor-crosslinked tissue specimen to an aqueous crosslinking bath for a predetermined time, such cross linking bath containing a liquid phase of a crosslinking agent selected from the group consisting of aldehydes, epoxides, isocyanates, carbodiimides, isothiocyanates, glycidalethers, and acyl azides. Such tissue may be porcine, ovine, equine or bovine in origin and preferably the initial material is taken from a bovine animal 30 days old or less, although tissue from older animals is contemplated as within the scope of the invention. In one preferred embodiment, the tissue specimen is subjected to chemical dehydration/compression and mechanical compression before cross-linking.

Pre-digestion is provided by digesting a harvested, cleaned pericardial tissue in a solution containing a surfactant, such as 1% sodium laurel sulfate. The chemical dehydration/compression step comprises subjecting the tissue specimen to hyperosmotic salt solution. And, the mechanical compression may be performed by subjecting the tissue specimen to a roller apparatus capable of compressing the tissue specimen to a thickness ranging from about 0.003' (0.0762 mm) to about 0.010" (0.254 mm).

The animal collagen tissue specimen is then chemically cross-linked first by exposing the tissue to formaldehyde vapor for approximately 10 minutes, and second by immersing the tissue in a glutaraldehyde solution for two consecutive sessions of approximately 24 hours each.

Retrieval System

In another embodiment, a retrieval system is contemplated for quickly removing the prosthetic valve during an aborted surgical deployment using minimally invasive cardiac catheter techniques. In this embodiment, the tethers would be captured by a catheter having a snare attachment. Once the tethers were captured, an intra-ventricular funnel attachment would guide the prosthetic valve into a collapsed, compressed conformation by pulling on the tethers, thus pulling the compressed prosthetic valve into the removal catheter for subsequent extraction.

To better assist understanding of the inventive subject matter, the following terms are given a more detailed definition.

DESCRIPTION OF FIGURES

Referring now to the FIGURES, FIG. 1 shows one embodiment of a prosthetic heart valve 110 according to the present invention, comprising tubular stent 112 having tether attachment structures 114 at one end and tubular stent 112 is attached to cuff 116 at the other end. Leaflet assembly 118 (not shown) is disposed within stent 112 and supports leaflets 120 (also not shown). Cuff 116 has independent articulating loops of wire 122 and covering 124.

As stated, tubular stent 112 may be an expandable laser cut stent or an expandable braided stent. Tubular stent 112 may be constructed of Martensitic or super clastic metal alloys. Tubular stent 112 may be compressed along its longitudinal axis and will fit into a catheter-based stent delivery system. When the tubular stent 112 is delivered to the location where it is to be installed, it is expelled from the catheter by an obturator and deposited at the site where it is to be deployed.

Tubular stent 112 includes a plurality of tether attachments 114 upon which a tether (not shown) may be connected. FIG. 1 shows an embodiment having three tether attachments which are integrated into the distal portion of the stent 112.

Leaflet assembly 118 is a separate but integrated structure that is disposed within the stent 112. Leaflet assembly 118 functions to provide the structure upon which the valve leaflets or cusps 120 are located. Leaflet assembly 118 may be made entirely of stabilized tissue or it may be a combination wire and tissue structure. Where leaflet assembly 118 is composed entirely of tissue, it is contemplated that the leaflet assembly, leaflet support structure, and leaflets or cusps 120 are made from tissue. It is contemplated as within the scope of the invention that different qualities of stabilized tissue, i.e. thin or thick, structurally rigid or flexible as it may be, may be used for the different components of the cuff covering 124, the stent covering, the leaflet assembly 118 and the leaflets 120. Where leaflet assembly 118 is composed of wire and tissue, it contemplated that assembly or support(s), or both, may be made from wire, and the cusps 120 would necessarily be made from tissue.

Prosthetic heart valve 110 also includes cuff 116. FIG. 1 shows cuff 116 formed from a cuff wire form 122 that is covered by, in one embodiment, stabilized tissue 124. In one embodiment, the cuff wire form is an extension of the stent itself, where the stent has been heated and manipulated upon a form to create the extended spindles of the flat, collar plate of the cuff. In another embodiment, the cuff wire form 122 is made separate from the stent 112 and attached as a flat collar plate constructed to include an inner rim 130 and an outer rim 132, with independent loops of wire 122 that create lobes or segments extending axially around the circumference of the inner rim, the joint 130 where the cuff 116 meets the tubular stent 112.

Figures 2A, 2B, 2C, 2D:
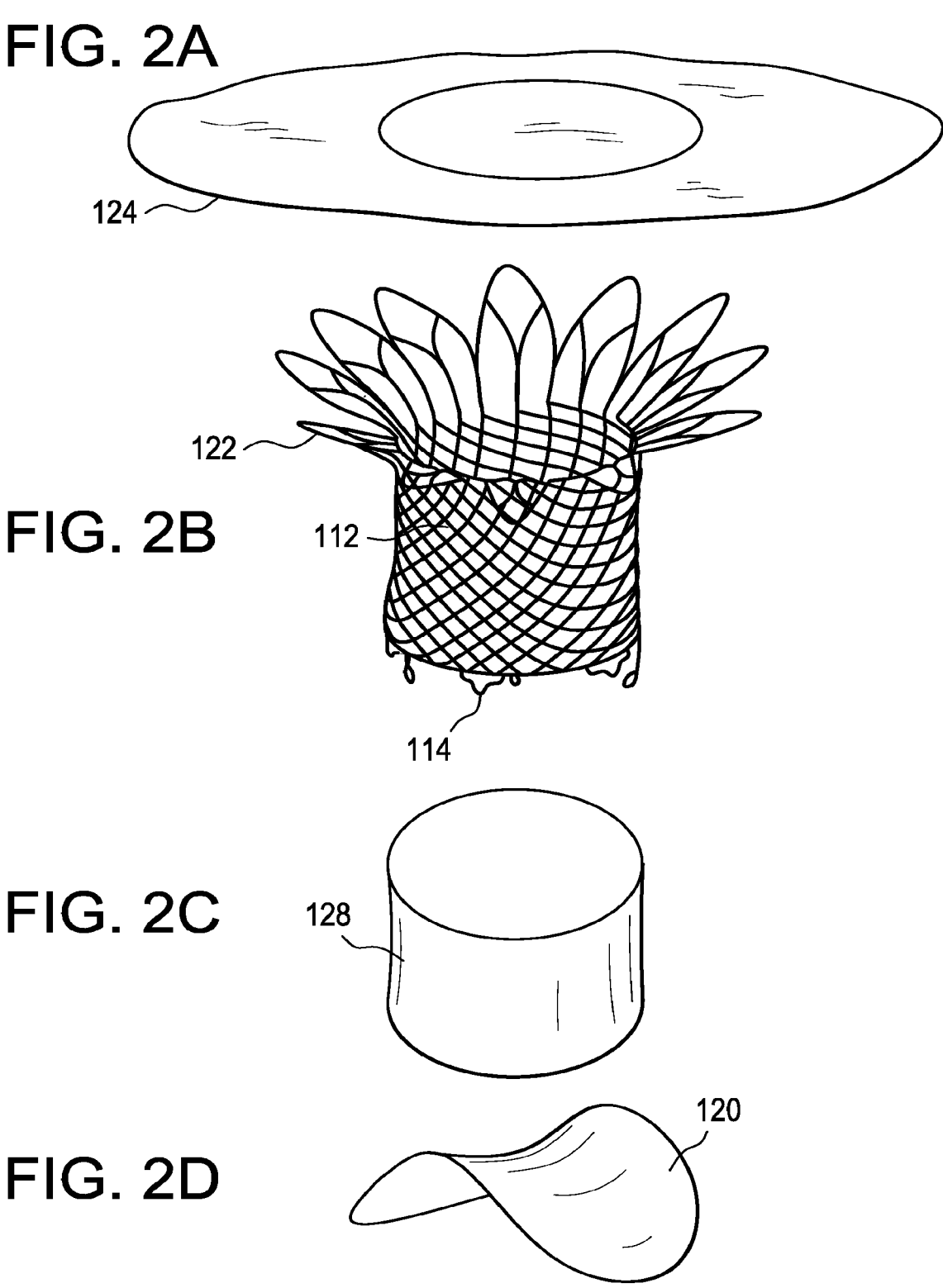
FIGS. 2 A-D is a perspective exploded view of one embodiment of a prosthetic valve according to the present invention that does not use a structural wire support for the valve cusps/leaflets.

Referring now to FIG. 2, an exploded component view is provided that shows cuff covering 124 in FIG. 2A. In FIG. 2B, the wire cuff loops, or spindles, 122, is illustrated along with stent body 112 and tether attachments 114. The combination of the stabilized tissue of the cuff covering 124 and wire cuff spindles, make up a cuff structure and provide a semi-rigid form that assists in the sealing of the cuff against the atrial trabeculations and tissue within and adjacent to the mitral annulus.

Referring to the stent body, it is contemplated as within the scope of the invention to include both laser cut stent technology and/or the braided stent technology. Where the cuff wire form 122 is merely an extension of a braided stent and forms a unitary stent-cuff construction, the spindles are formed by heating a Nitinol (IM) stent on a mold to create the proper extension and angle necessary to establish the cuff or collar portion.

Where the stent is laser cut, the cuff wire form 122 may be manufactured as a unitary laser-cut stent-cuff construction. In this embodiment, the cuff wire form and the stent are laser cut within the same overall manufacturing process. Where the cuff wire form is made separate from the stent and attached as a flat collar plate, the cuff wire form and stent may be manufactured/laser cut separately and attached using laser weld or other similar technique to create a non-fatiguing elastic stent-cuff joint capable of maintaining elastic compliance while it is deployed.

As noted, the rim may consist of an artificial transition point between the stent and the cuff where the stent has been heated to change the shape and angle of the topmost portion of the stent or the valve has been laser cut to create its overall wire form, or the rim may consist of a constructed transition point such as a laser welded joint for attaching two component parts.

Once the cuff is covered by stabilized tissue 124, the loops 122 provide the cuff 116 the ability to travel or flex up and down, along the longitudinal axis; longitudinal defined by the lengthwise axis of the stent. As stated, this flexibility or compliance provides the prosthetic heart valve, specifically the cuff, upon being deployed within a patient's heart, the ability to conform to the anatomical shape of the left atrium, maintain the conforming shape during the cardiac cycle, and provide a tight seal against the atrial tissue adjacent the mitral valve aperture. This feature reduces or removes the guesswork that often accompanies the pre-surgical sizing of a mitral valve. By providing a better fit, this necessarily prevents blood from leaking around the implanted prosthetic heart valve.

The cuff tissue 126 is thin, durable, and may be attached to the top, bottom, or both sides of the cuff 116.

Referring now to FIG. 2C is a stent liner 128 made from tissue and that may optionally function to support the leaflets of the valve. This liner is contemplated as being made of tissue or biocompatible material as disclosed herein. The stent may also optionally have an inner stent liner and/or an outer (surface) stent liner. FIG. 2D is a perspective view of one embodiment of a two-piece structure made of leaflets 120. In this embodiment, the leaflet structure is illustrated in a prosthetic heart valve having a mitral valve shape, a "saddle shape" that constitutes a hyperbolic paraboloid to afford one specific form of structural integrity.

Figure 3A:
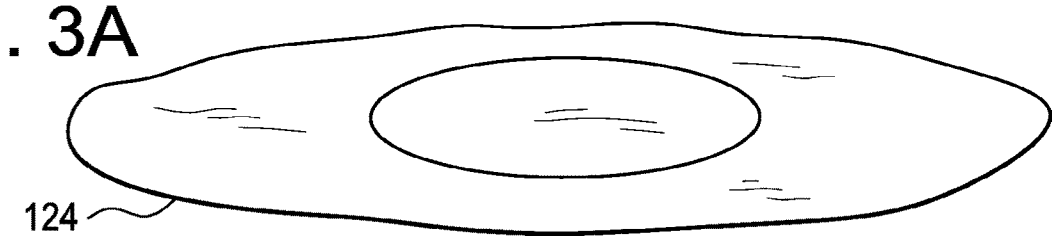
FIGS. 3 A-E is a perspective exploded view of one embodiment of a prosthetic valve according to the present invention that incorporates a structural wire support for the valve cusps/leaflets.
Figure 3B:
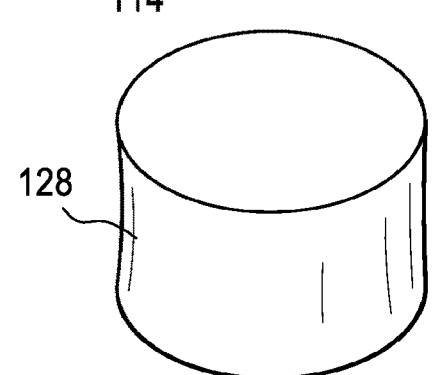
Figure 3C:
Figure 3D:

Referring now to the exploded view in FIG. 3 A-E, the cuff covering 124 is shown in FIG. 3A. The stent body 112 and cuff spindles 122 are shown in FIG. 3B. FIG. 3C shows a stent liner 128 made from tissue and that may optionally function to support the leaflets of the valve. FIG. 3D is a perspective view of one embodiment of a two-piece structure made of leaflets 120, and illustrated in a prosthetic heart valve having a mitral valve shape, a "saddle shape".

Figure 3E:
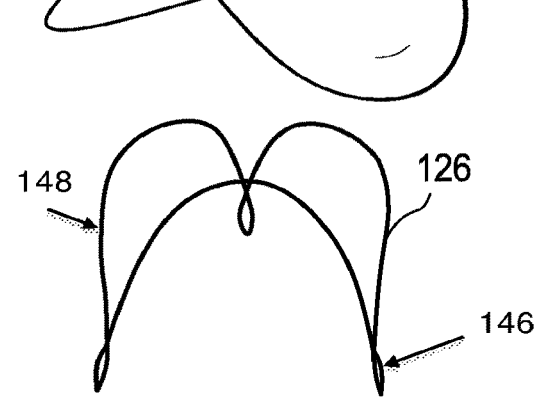

FIG. 3E shows the use of a structural wire support 126 for the leaflets 120. This leaflet structural wire support also provides spring-like tension to assist in the proper orientation of the leaflets once the prosthetic heart valve is expanded from a compressed stored shape to its final functional shape. FIG. 3E shows the three junctions 146 (commissural tips) and the three arched wires 148 (of this embodiment) of the leaflet structural wire support 126. Leaflet wire form is preferably constructed as a single wire that is molded, twisted, and/or manipulated into the final shape. In another embodiment, the leaflet wire form is series of wires that have been attached, e.g. laser welded. In one embodiment, the junctions 146 move independently of the stent. Specifically, the junction end of the leaflet assembly may not be attached to the stent, but only the upper portion. Having unattached junctions with the ability to flex inward and, more importantly, expand outward, gives the leaflet wire form the structural ability to collapse when compressed and expand when deployed. The ability to compress and expand independently of one another, relieves mechanical stresses on the tissue.

Figure 4:
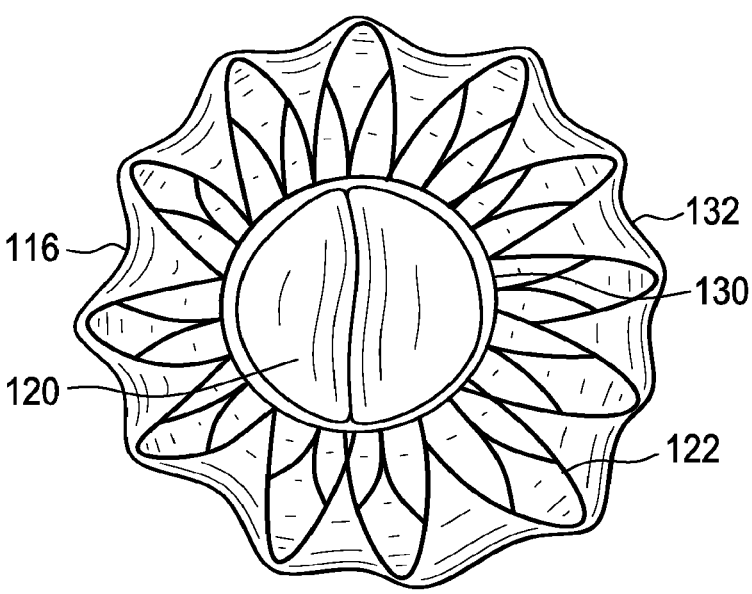
FIG. 4 is a top view of an embodiment of a prosthetic valve according to the present invention and shows a two-leaflet structure.

Referring now to FIG. 4, FIG. 4 shows inner rim 130 and outer rim 132 of cuff 116. Spindles 122 are shown between the outer rim 128 and the inner rim 130. Valve leaflets 120 are shown within the inner rim 130.

Figure 5:
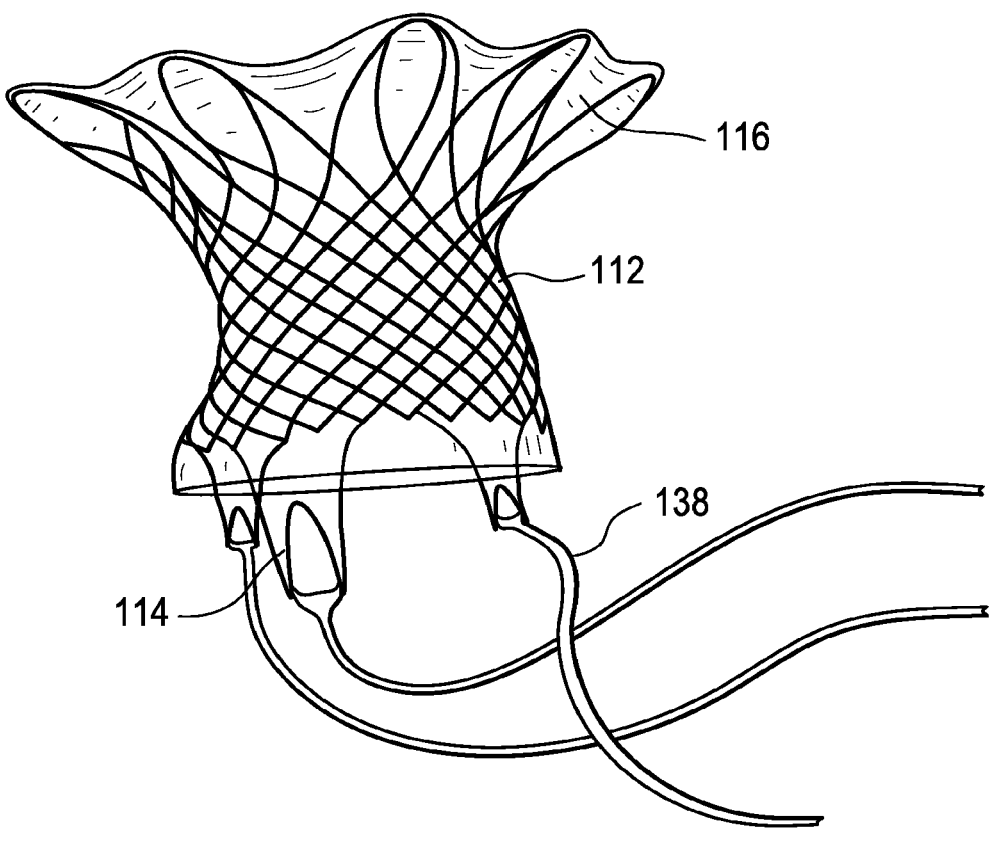
FIG. 5 is a side view from slightly below the horizontal plane of one embodiment of a prosthetic valve according to the present invention to show the bottom surface of the cuff.

FIG. 5 shows a side view from slightly below the horizontal plane of one embodiment of a prosthetic valve according to the present invention to show the bottom surface of the cuff. FIG. 5 shows stent 112 having three tether attachment structures 114 projecting from the distal end of stent 112 for attaching to tethers 138.

FIG. 5 shows an example of an embodiment wherein the cuff 116 is formed from the stent 112 by heating and shaping.

Figure 6:
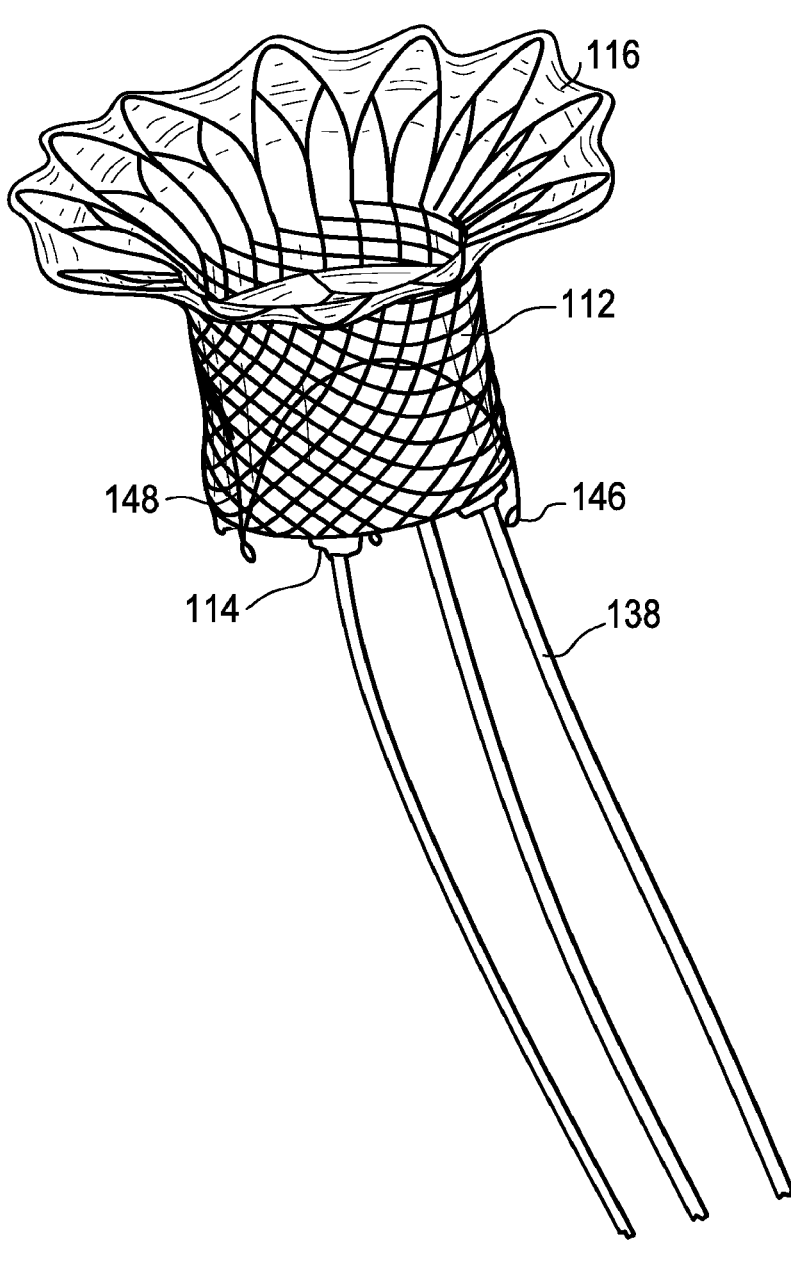
FIG. 6 is a top view from slightly above the horizontal plane of one embodiment of a prosthetic valve according to the present invention and shows the top surface of the cuff and structural wire support loops extending beyond the length of the stent.

FIG. 6 shows an example of an embodiment wherein the cuff 116 and stent 112 are formed from two joined pieces. FIG. 6 also shows that tethers 138 are not attached to the leaflet assembly or leaflet wire form 148 and 146 (shown for illustration purposes but would not be visible through tissue or synthetic material, e.g. liner), but rather the tethers 138 are contemplated as attaching to the stent 112, to the base of the cuff 116, to an upper portion of the cuff 116, or a combination of the above.

Figure 7:
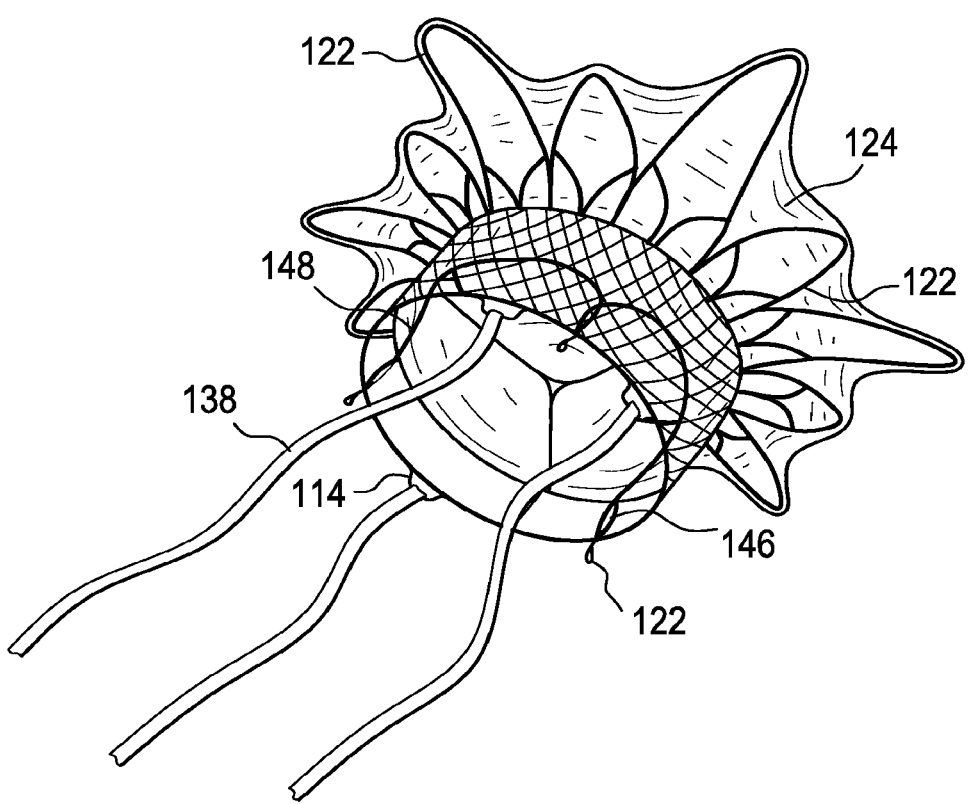
FIG. 7 is a view of one embodiment of a prosthetic valve according to the present invention showing that the cuff spindles may optionally have variable lengths and sizes.

Referring now to FIG. 7, there is shown an example of where the cuff spindles may vary in design size and shape. FIG. 7 shows a completely expanded prosthetic valve 110 fully expelled from the flexible delivery catheter, including cuff wire form 122, cuff tissue covering 124, tethers 138, tubular stent 112, sealed joint 170, tether attachment 114, and tethers 138. FIG. 7 illustrates where every other spindle is longer than the adjacent showing an alternating pattern. This provides an advantage of additional coverage and compliance of various cuff designs, in combination with how tethers 138 are pulled and shortened to adjust or move the prosthetic valve towards and within the valvular annulus where it will be seated, adjusted, and fastened in place to complete the deployment. FIG. 7 also shows that tethers 138 are not attached in this embodiment to the leaflet assembly or leaflet wire form 148 and 146 (shown for illustration purposes but would not be visible through tissue or synthetic material, e.g. liner).

Figure 8:
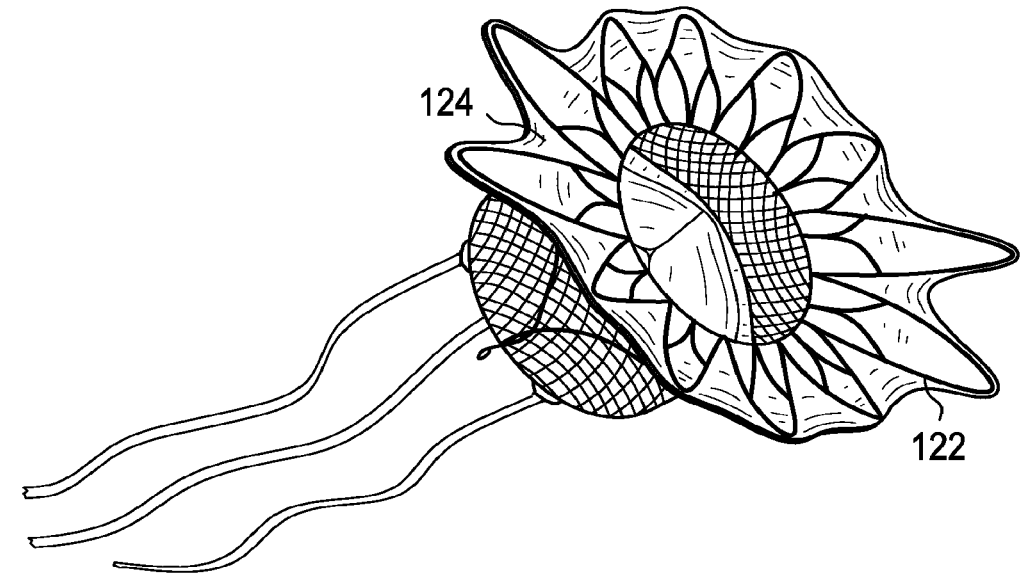
FIG. 8 is a view of one embodiment of a prosthetic valve according to the present invention showing that the cuff spindles may optionally have variable lengths and sizes. Here they are shown to create an elongated cuff.

FIG. 8 shows another variation of one preferred embodiment of the present invention where the spindles do not alternate, but rather two spindles on either side create an elongated cuff for a prosthetic valve where this provides an advantage. Sealed joint 170 is shown where the stent body connects to the cuff.

Figure 9:
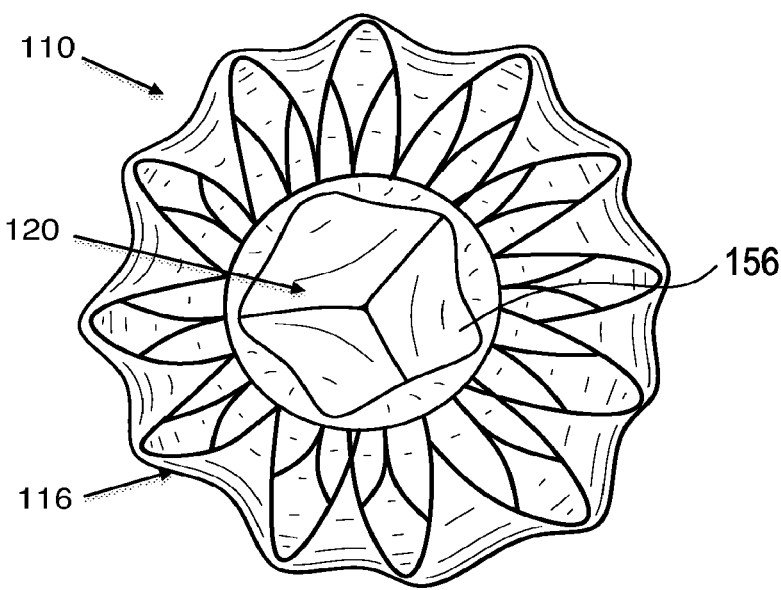
FIG. 9 is a top view of one embodiment of a prosthetic valve according to the present invention showing a three-leaflet structure.

FIG. 9 shows a top view of a three-leaflet structure 156 as though from inside the left atrium looking down toward the left ventricle, and shows the completely expanded prosthetic heart valve 110 seated and adjusted to form a tight seal within the mitral annulus. FIG. 9 also shows valve leaflets 120, cuff 116, and independent loops of wire 122.

Figure 10A:
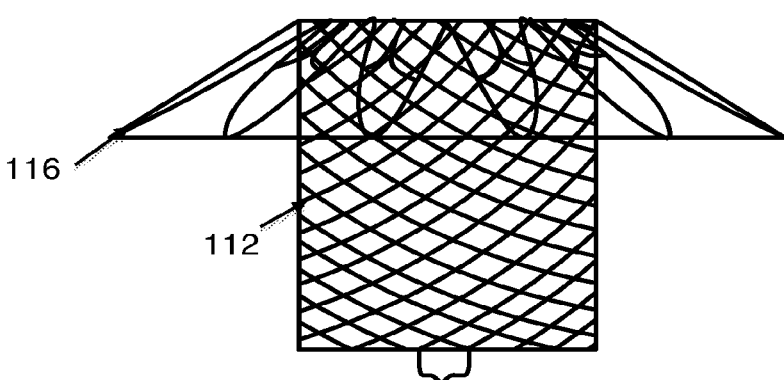
FIG. 10 A-C is a series of side views of one embodiment of a prosthetic valve according to the present invention illustrating that the cuff may be formed to have an original configuration whereby the cuffs disposition relative to the stent body has an acute, right, or obtuse angle.
Figure 10B:
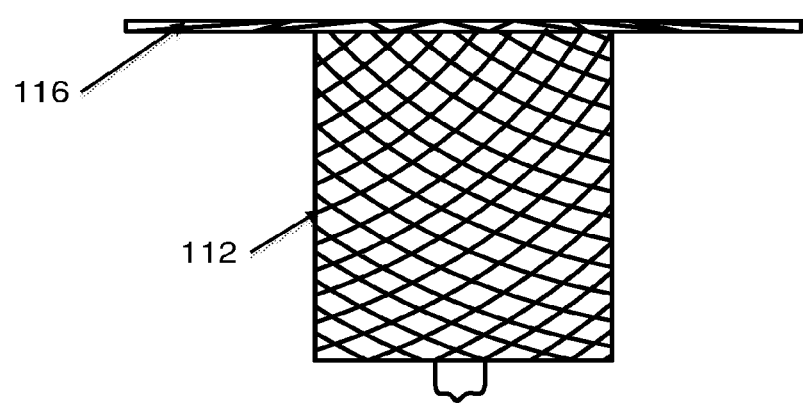
Figure 10C:
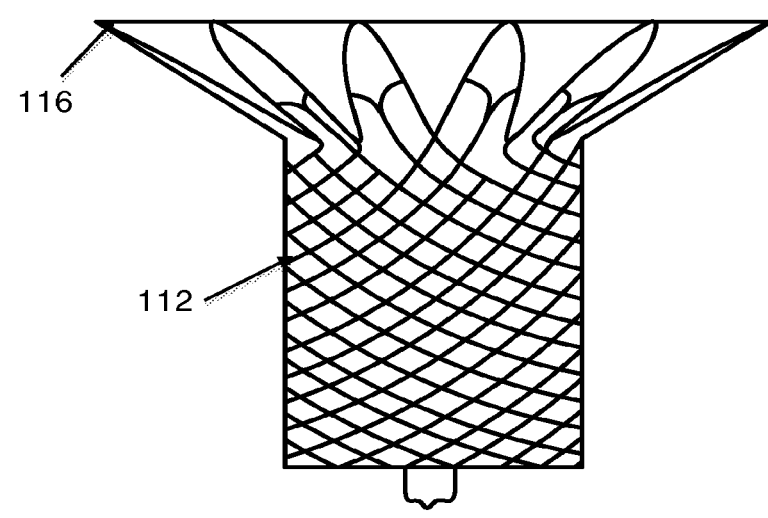

Referring now to FIG. 10, there is provided an illustration of how the cuff and stent body may be formed in such a manner to create various positions, e.g. angles, for the cuff. The angular relationship between the cuff 116 and the stent 112 function to seal the prosthetic heart valve against the mitral valve aperture and prevent leaking. In one embodiment, FIG. 10A, the angle of the cuff may also include a more acute inverted-funnel shaped angle. Although not limiting, in one example, the angle is 60 degrees. FIG. 10B illustrates the angle of an approximately perpendicular angle. FIG. 10C illustrates a more obtuse funnel-shaped angle, e.g. 150 degrees, in relation to the longitudinal axis of the stent.

Figure 11:
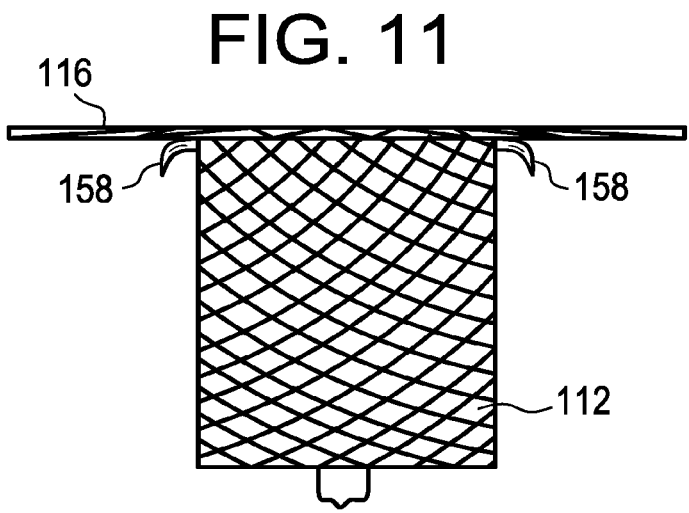
FIG. 11 is a side view of one embodiment of a prosthetic valve according to the present invention illustrating the use of a barb component to assist seating the prosthetic valve in the valvular annulus.

FIG. 11 shows how tines or barbs can facilitate the attachment to the tissue, such as the mitral annulus or the tricuspid, annulus. FIG. 11 shows cuff 116 attached to stent body 112 where barbs 158 have been attached at the neck of the prosthetic valve where the cuff meets or transitions to the stent body.

Figure 12A:
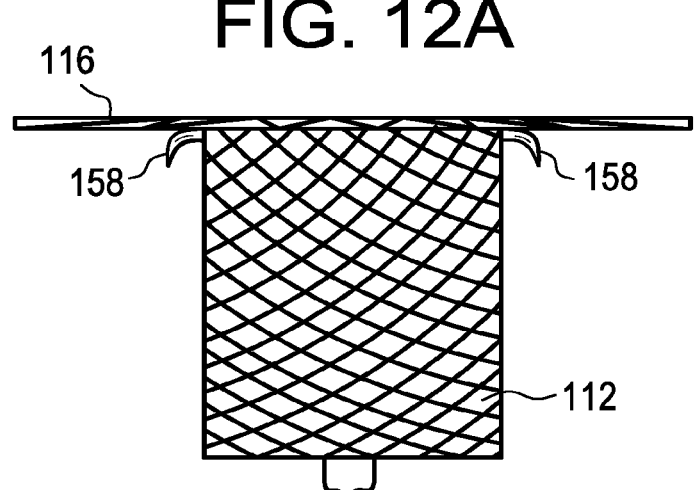
FIG. 12 A-B is a pair of side views of one embodiment of a prosthetic valve according to the present invention illustrating the use of a barb component which is open but then closes upon or into the annular tissue when the stent body is expanded to assist seating the prosthetic valve in the valvular annulus.
Figure 12A:
Figure 12B:
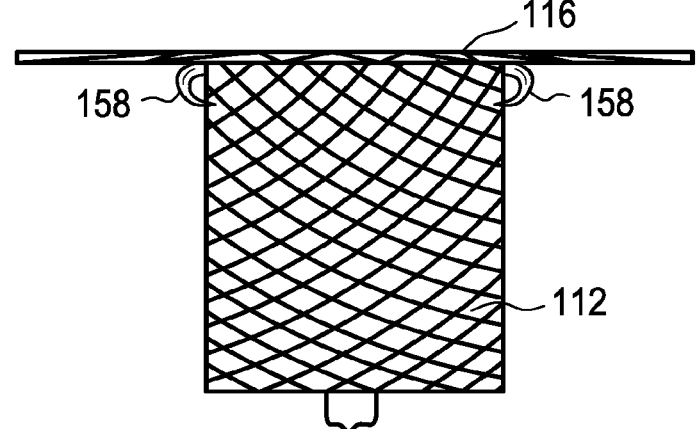

FIG. 12 A-B illustrates a specific form of hooked barb 158 where the hooked barb is adjusted to provide an opening between the barb and the stent body where an operator would direct the annular tissue to assist with seating the valve. Upon placing the prosthetic valve 110 there, a balloon catheter or other expansion means is inserted into the stent 112 to expand the internal diameter, thus causing the hooked barbs 158 to rotate back inwards toward the stent 112, thus capturing and locking the annular tissue to the stent body.

Figure 13:
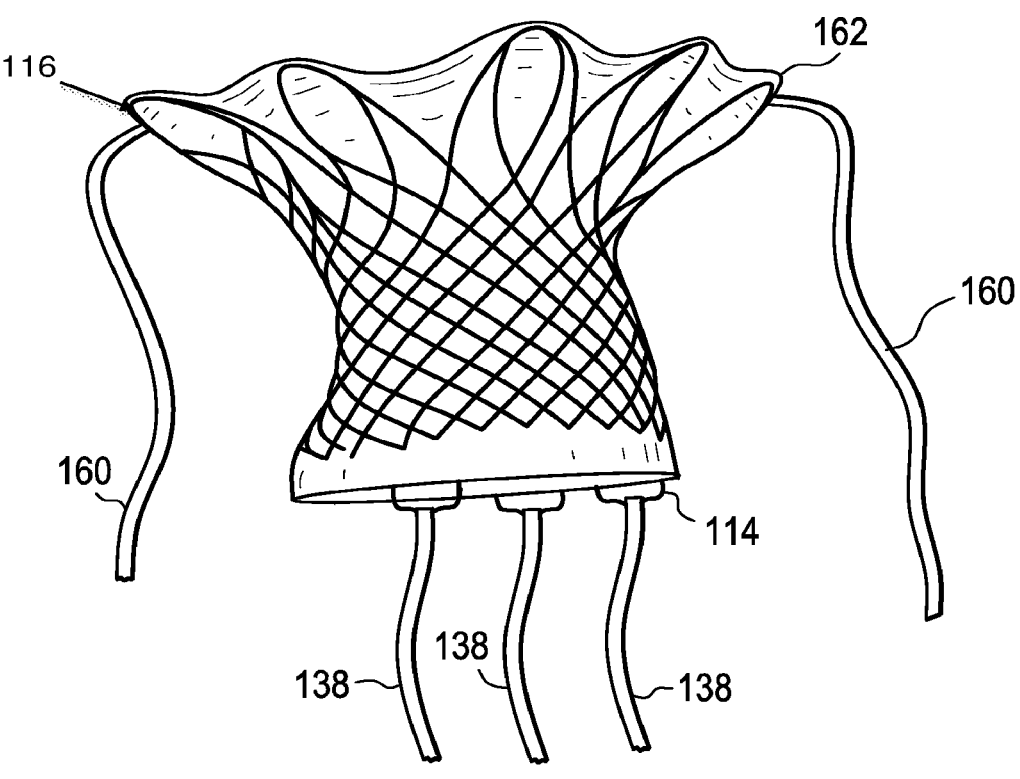
FIG. 13 is a side view of one embodiment of a prosthetic valve according to the present invention showing tethers attached to the cuff portion in addition to attachment on the stent body.

FIG. 13 shows a prosthetic valve according to the present invention showing tethers 160 attached to the cuff portion 116 with optional cuff-tether attachments 162 in addition to attachment 114 of the tethers 138 on the stent body. By providing the surgeon the ability to control, adjust, tighten, the cuff geometry relative to the stent geometry, many options are provided that were not heretofore known to be available in the prior art.

Figure 14:
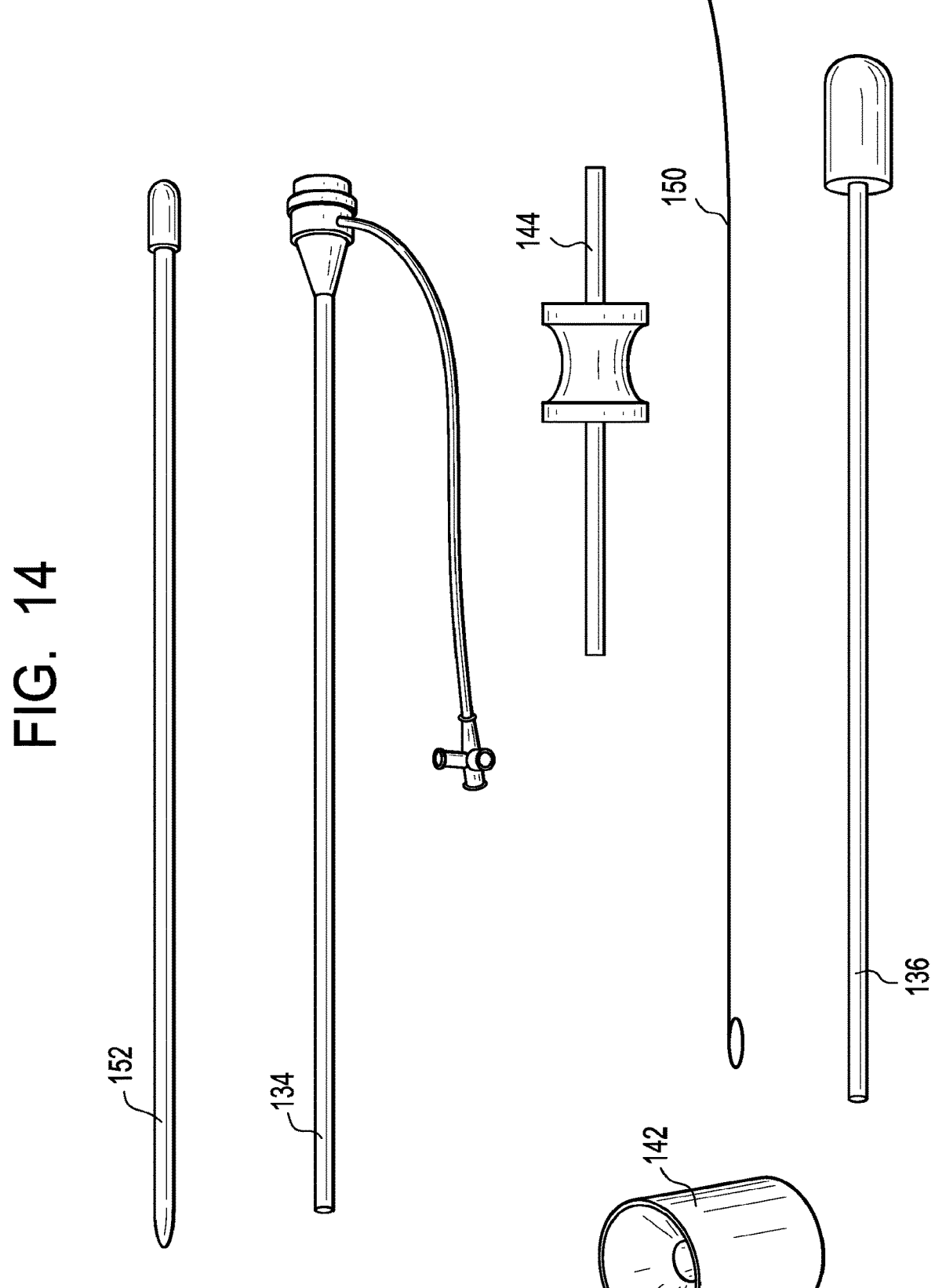
FIG. 14 is a drawing of one embodiment of the delivery system equipment according to the present invention used to compress and deploy the prosthetic valve.

Referring now to FIG. 14, this is a drawing of one preferred embodiment of equipment as claimed herein that is used to compress the prosthetic valve and insert the prosthetic valve into the heart. FIG. 14 shows funnel compressor 142, introducer 144, snare 150, flexible deployment catheter 134, catheter insert 152, and obturator 136, the implementation of which is further described in FIG. 15.

Figure 15A:
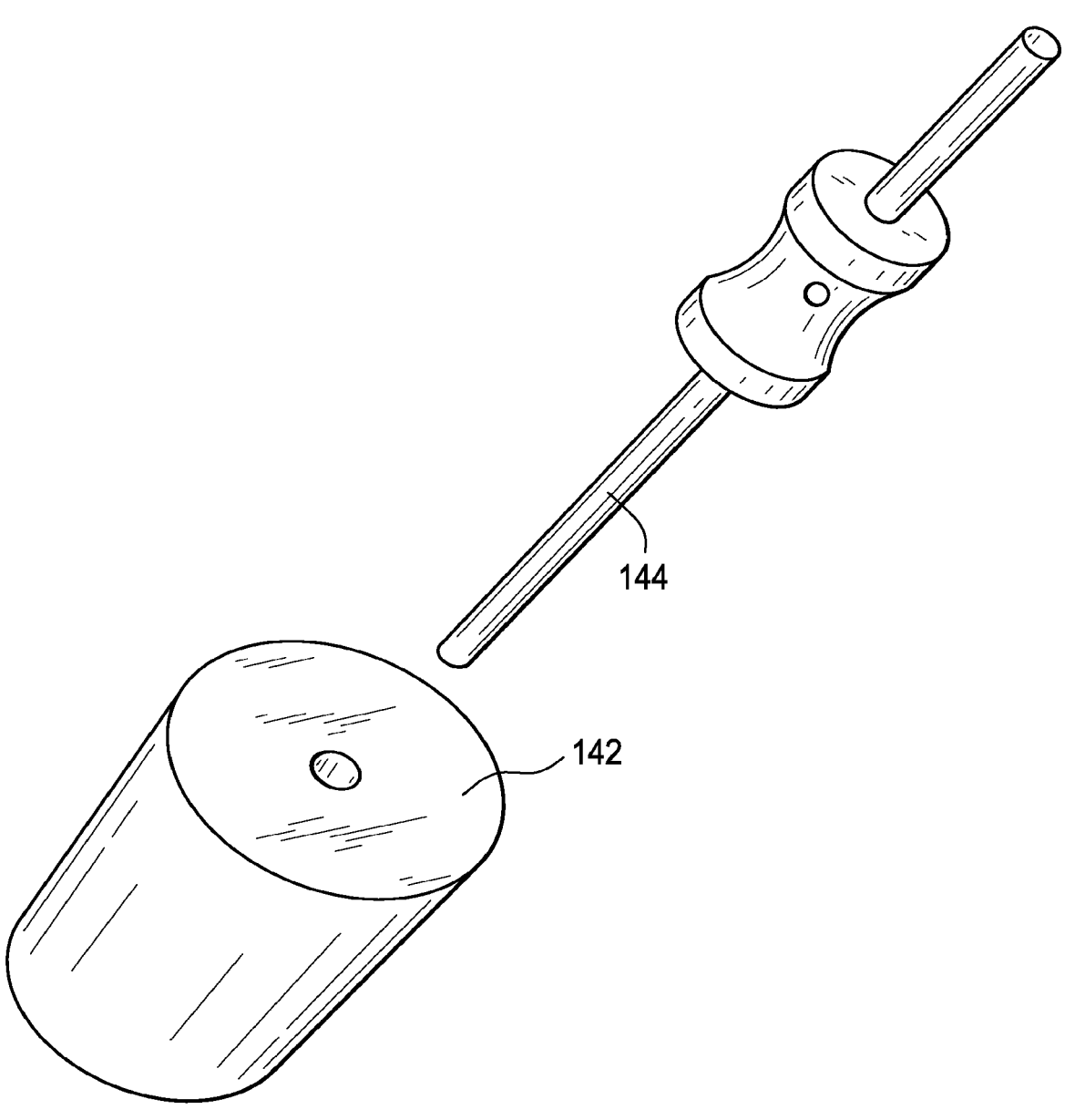
FIG. 15 A-F is a series of drawings of one embodiment of the delivery system according to the present invention.
Figure 15B:
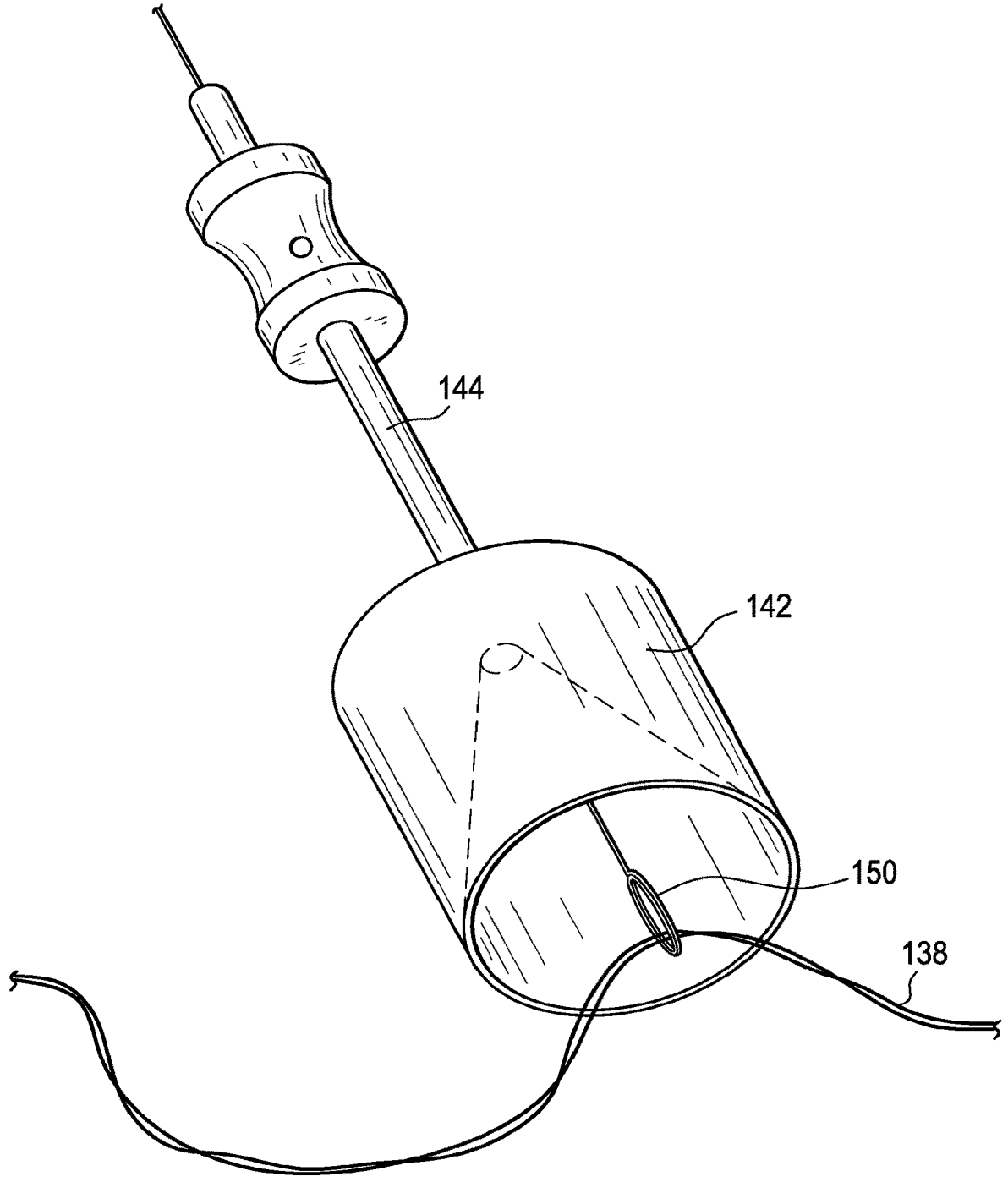
Figure 15C:
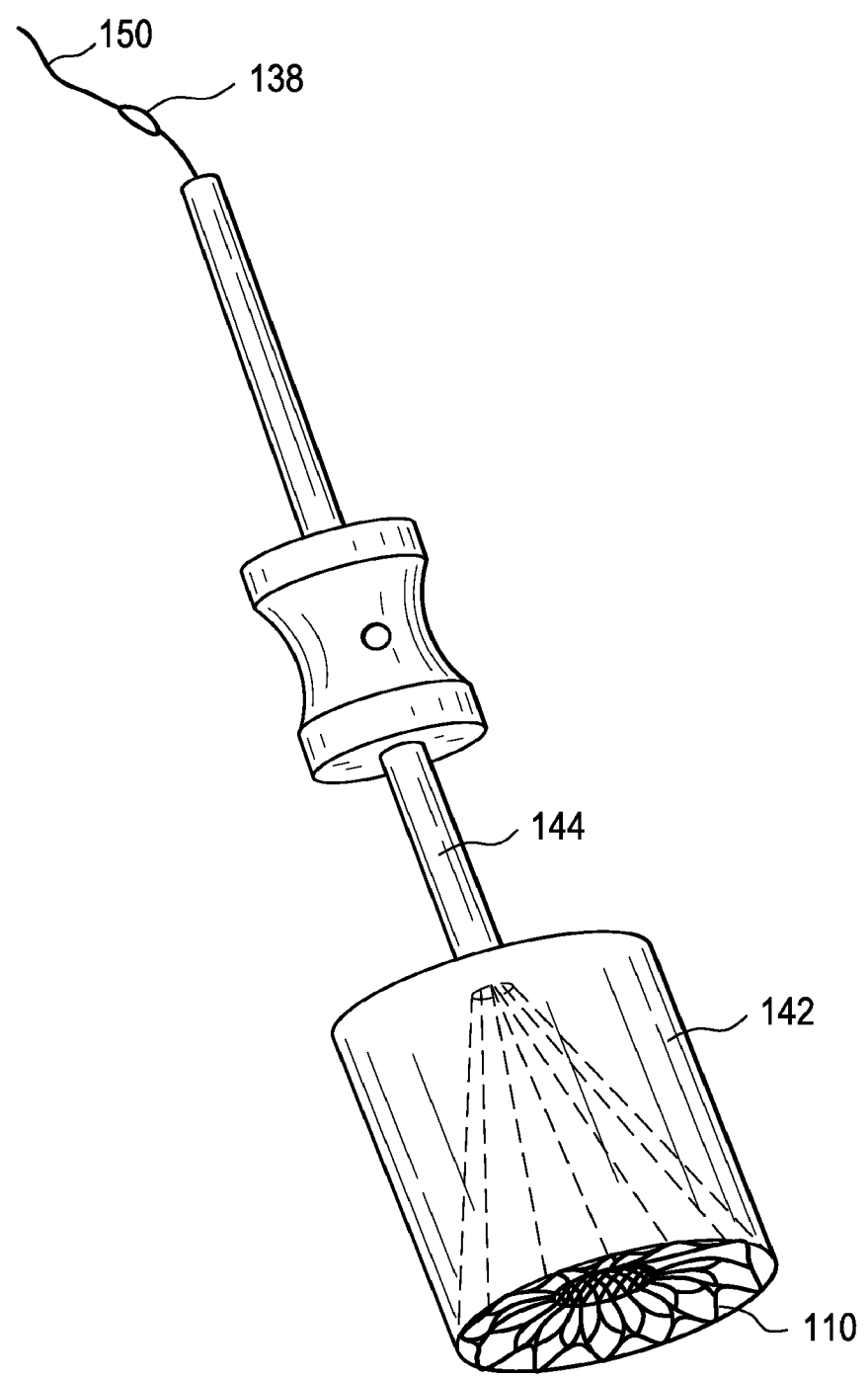
Figure 15D:
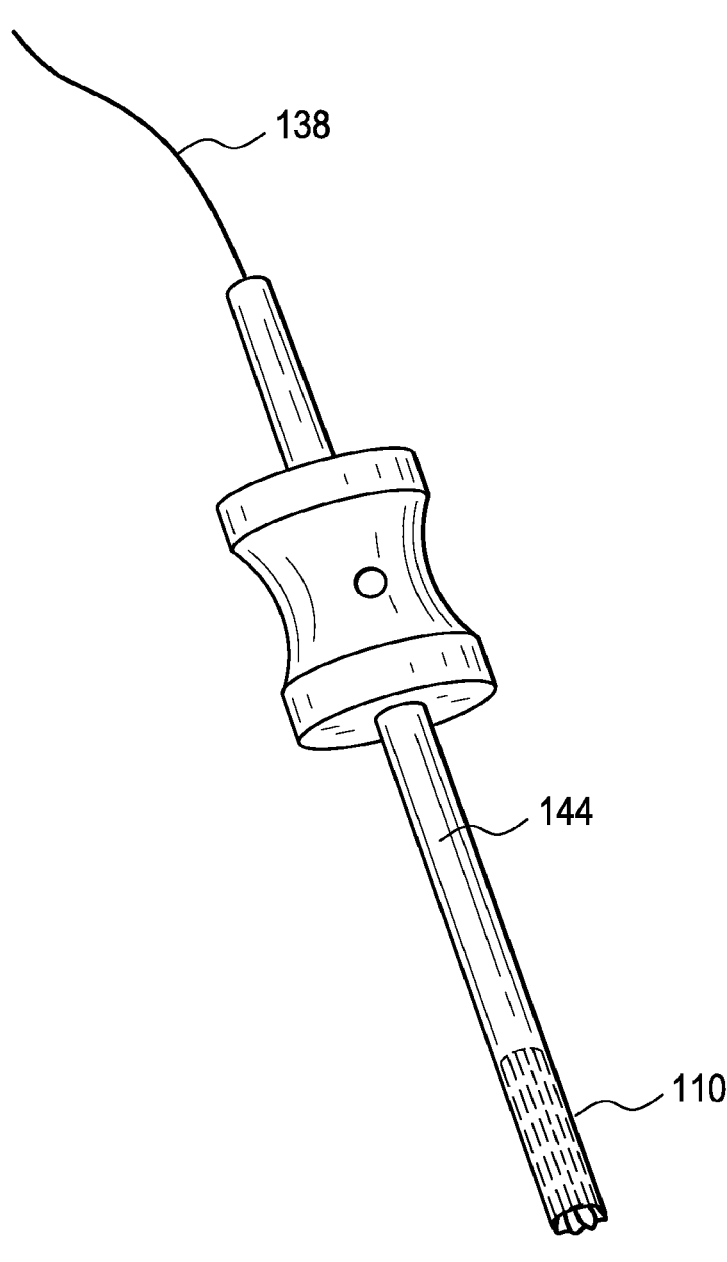
Figure 15E:
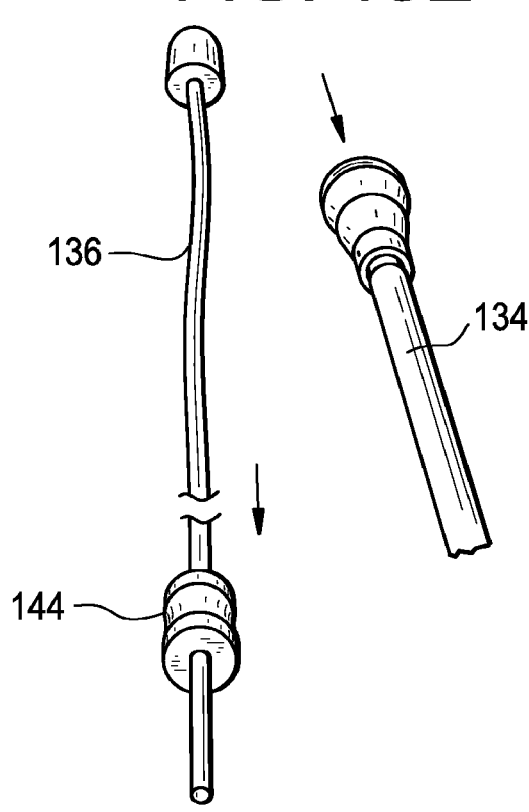
Figure 15F:
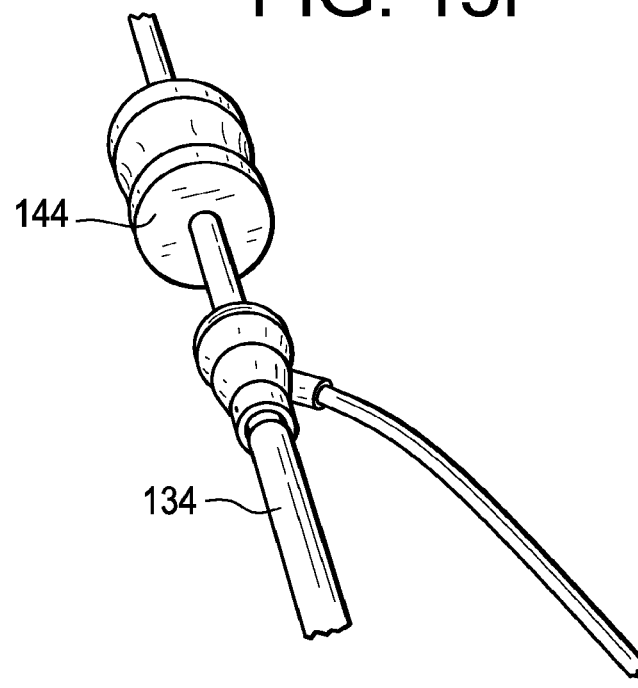

Referring now to FIGS. 15A-F is a series of drawings of one embodiment of the assembly of a delivery system for a prosthetic valve according to the present invention. FIGS. 15A-F show the preparation of the prosthetic valve for implantation into the heart by showing how the prosthetic valve is loaded into the flexible delivery catheter. FIG. 15A shows the initial step of attaching the introducer 144 to the compression funnel 142. FIG. 15B shows the snare 150 pulling tethers 138 into compression funnel 142 and threading through introducer 144. FIG. 15C shows the prosthetic valve 110 just prior to being drawn into the compression funnel 142 as it is pulled rear-ward using tethers 138 into introducer 144. FIG. 15D shows the prosthetic valve 110 (not shown) inserted into the introducer 144 with the anchoring tethers 138 extending from the rear of the introducer 144. FIGS. 15E and 15F show the flexible delivery (deployment) catheter 134 being attached to the introducer 144 to introduce, or insert, the compressed prosthetic valve 110 (not shown) into the flexible delivery catheter 134. In summary, FIG. 15 shows prosthetic valve 110 with tethers 138 that have been threaded, using a snare 150, through the funnel compressor 142 which is attached to introducer 144. Upon pulling the tethers 138, the prosthetic valve 110 is mechanically compressed by the funnel 142 and inserted into the introducer 144. The introducer 144 is then inserted into the delivery catheter 134 in preparation for loading the delivery catheter. The obturator 136, having diameter slightly less than the introducer and the delivery catheter, is then inserted into the rear portion of the introducer and pushes the compressed and tethered prosthetic valve into the delivery catheter. It is contemplated that this process will be performed in the operating room just prior to installing the valve in the patient. In another embodiment, a ready-made pre-filled catheter/valve delivery system is provided.

Figure 16:
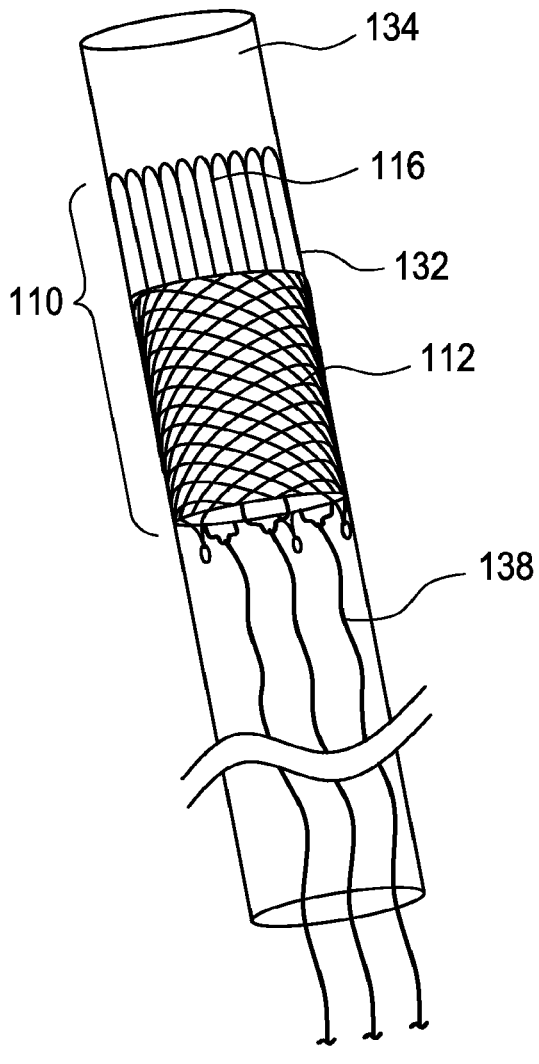
FIG. 16 is a detailed sectional view of an embodiment of a delivery catheter, and one embodiment of a compressed prosthetic valve according to the present invention disposed within the delivery catheter.

Referring now to FIG. 16 is a detailed sectional view of the catheter delivery system 132, which includes the compressed prosthetic valve 110 according to the present invention disposed within the delivery catheter 134. FIG. 16 shows prosthetic valve 110 having cuff 116 attached to stent 112, which further has tethers 138 leading away from the compressed valve 110.

Figure 17:
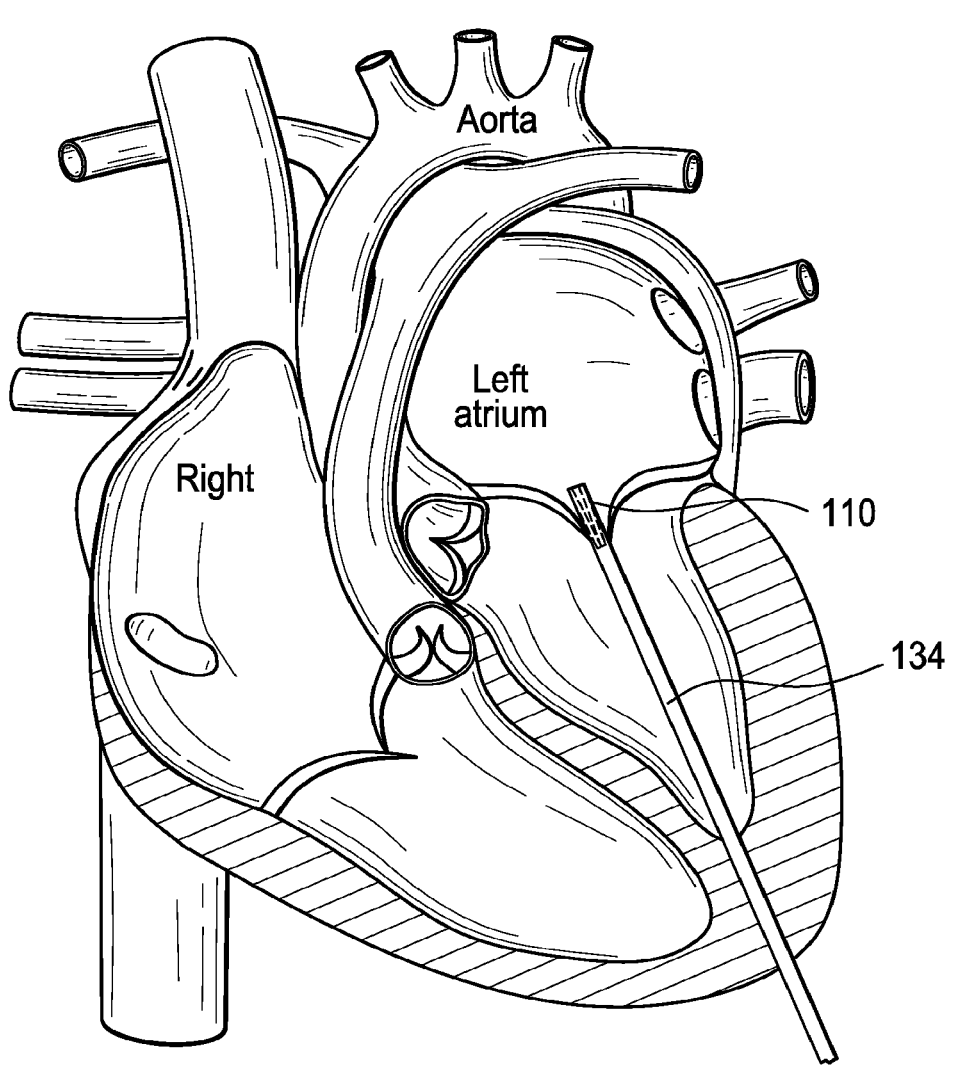
FIG. 17 is a cut-away view of a heart with a delivery catheter containing a prosthetic valve according to the present invention and accessing the heart using an apical approach.
Figure 18A:
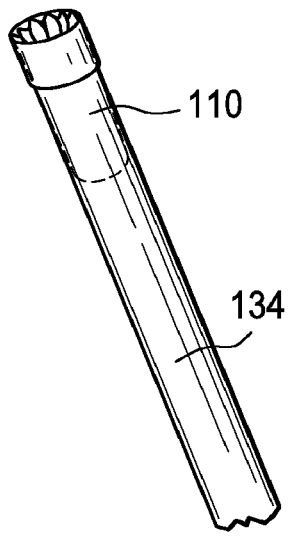
FIG. 18 A-D is a series of views of the tip of one embodiment of a delivery catheter according to the present invention containing a pre-loaded prosthetic valve which is being pushed out of the delivery catheter, i.e. by an obturator, starting with (A) the valve completely within the catheter, (B) the cuff portion being in view, (C) the stent body following, and (D) the prosthetic valve with attached tethers for positioning and/or adjustment and/or securing the valve to tissue.
Figure 18B:
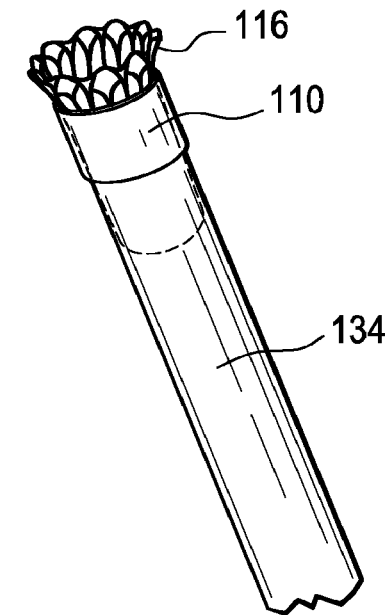
Figure 18C:
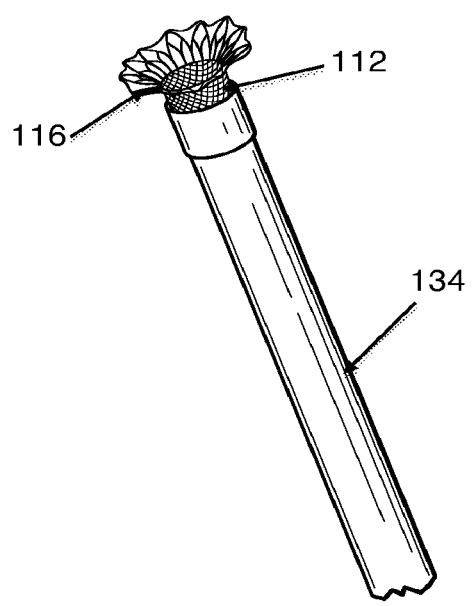
Figure 18D:
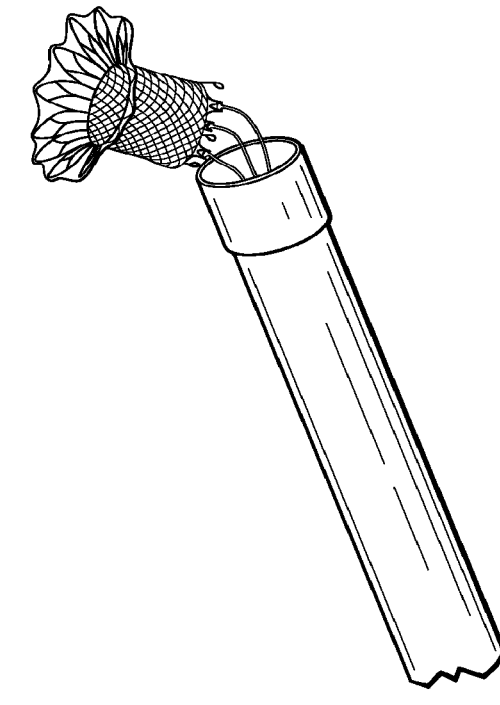

FIG. 17 is a cut-away view of a heart with a delivery catheter containing a prosthetic heart valve according to the present invention and accessing the heart using an apical approach. It is contemplated that other surgical approaches to the heart, and valves in addition to the mitral valve, are within the scope of the inventive subject matter claimed herein. FIG. 17 shows the delivery catheter 134 advanced to through the mitral valve and into the left atrium for deployment of the prosthetic valve 110.

FIG. 18 A-D is a series of drawings of the deployment of one embodiment of a prosthetic valve according to the present invention. FIG. 18 A-D is a series of views of the tip of one embodiment of a delivery catheter according to the present invention containing a pre-loaded prosthetic valve which is being pushed out of the delivery catheter, i.e. by an obturator, starting with (A) the valve completely within the catheter, (B) the cuff portion being in view, (C) the stent body following, and (D) the prosthetic valve with attached tethers for positioning and/or adjustment and/or securing the valve to tissue. FIGS. 18A-D shows how the prosthetic valve 110 is deployed from flexible deployment catheter 134. FIG. 18B shows the cuff 116 emerging from the catheter 134. FIG. 18C shows the cuff 116 and stent 112 partially expelled from the delivery catheter 134. FIG. 18D shows the prosthetic valve completely expelled from the delivery catheter 134 with tethers 138 attached to the stent body and trailing behind into the catheter. FIG. 18D further shows tethers 138 attached to the stent 112, with prosthetic valve 110 now expanded and delivered (but not positioned or adjusted), as the delivery catheter 134 is withdrawn away from the target location, e.g. atrium.

Figure 19:
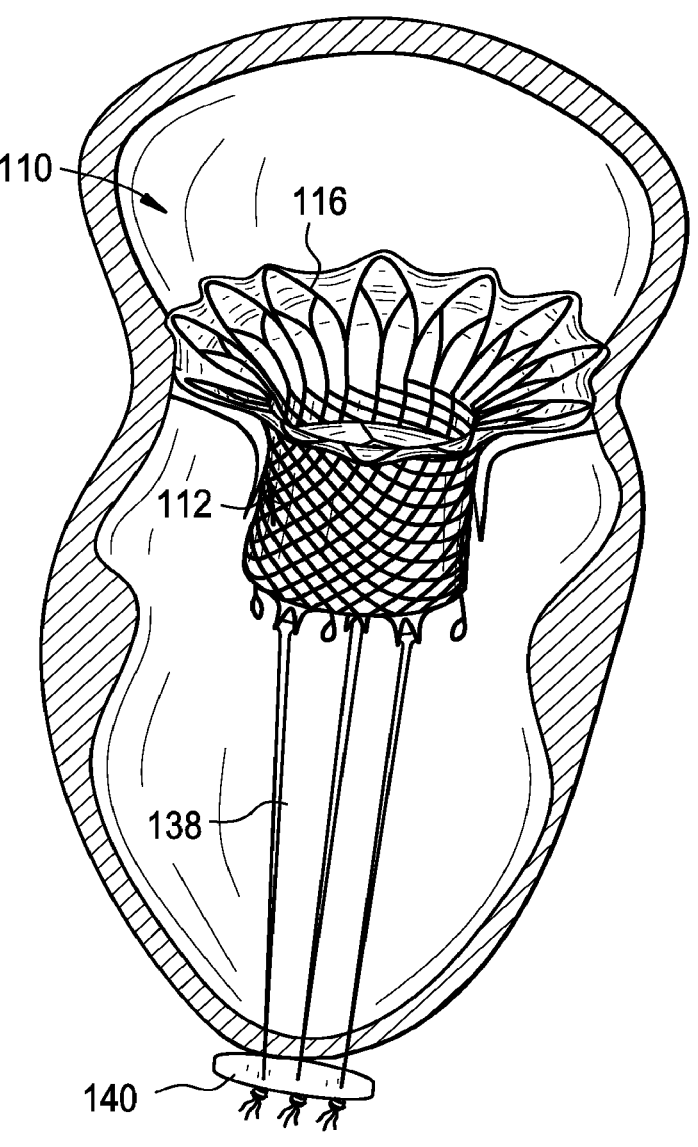
FIG. 19 is a detailed sectional view of one embodiment of a prosthetic valve according to the present invention deployed within the annulus of the mitral valve of the heart and shows that it is anchored using (a) the atrial cuff and (b) the ventricular tethers connected to the apex, which are shown secured by a securing pledget.

Referring now to FIG. 19, FIG. 19 shows a depiction of a fully deployed prosthetic heart valve 110 installed in the left mitral valve of the heart having the tethers 138 attached to the left ventricle apex of the heart. Tethers 138 in this embodiment extend through the heart muscle and are attached to securing device 140, here shown as a pledget placed on the epicardial surface and having tethers fastened thereto.

In this embodiment, the pledget 140 performs the function of an anchor to which the tethers 138 are attached. Tethers 138 are strung through the left ventricle apex and pulled downward to seat prosthetic valve 110 in the atrial valve area. The completely installed prosthetic valve is held in the left atrium by the cuff 116 and secured to the apex of the heart by tethers 138. The tethers may be held in place by a securing device which in this aspect of the invention is a pledget 140 that the tethers are threaded through and secured against, i.e. by tying a knot or using a cinching feature.

Figure 20:
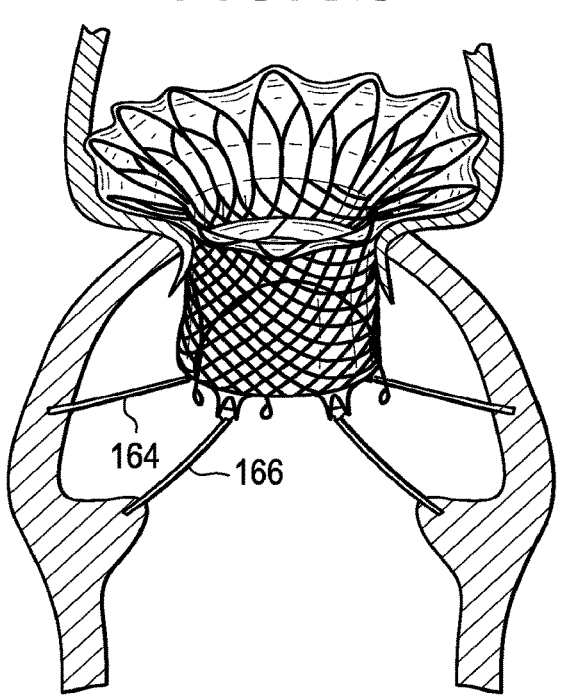
FIG. 20 is a detailed side-perspective view of one embodiment of a prosthetic valve according to the present invention deployed within the annulus of the mitral valve of the heart and anchored using (a) the atrial cuff and (b) the ventricular tethers connected to papillary muscles and/or ventricular wall and/or septum, which are each secured by one or more securing tissue anchors.

Referring now to FIG. 20 is a detailed cross-sectional view (of the heart) of one embodiment of a prosthetic heart valve according to the present invention deployed within the mitral valve aperture of the heart and anchored, in an alternative embodiment, between (A) where it is seated or lodged by the atrial cuff and (B) the ventricular tethers connected to papillary muscles 166 and/or ventricular wall and/or tether(s) attached to septum 164, which are each secured by one or more securing tissue anchors, anchoring devices, or anchoring methods.

Figures 21A, 21B:
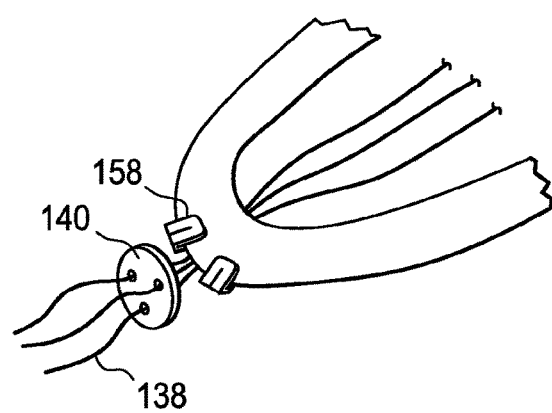
FIGS. 21 A-B is a pair of drawings showing one embodiment of a ventricular tether attachment according to the present invention.

FIG. 21A-B shows how the tethers 138 are tied off at the apex of the heart after deployment of the prosthetic valve 110. FIG. 21A shows the flexible delivery catheter 134 inserted into the left ventricular apex along with a suture 156 having partially installed apical-closure/tissue-buttressing material 158. FIG. 21B shows the anchoring system of the prosthetic valve in which the ventricular tethers 138 are shown treaded through the left ventricle apex and through a partially installed pledget 140; also shown are fully installed apical suture-closure material 156/158. Tissue buttressing material may optionally be in one embodiment a pledget felt.

Figure 22A:
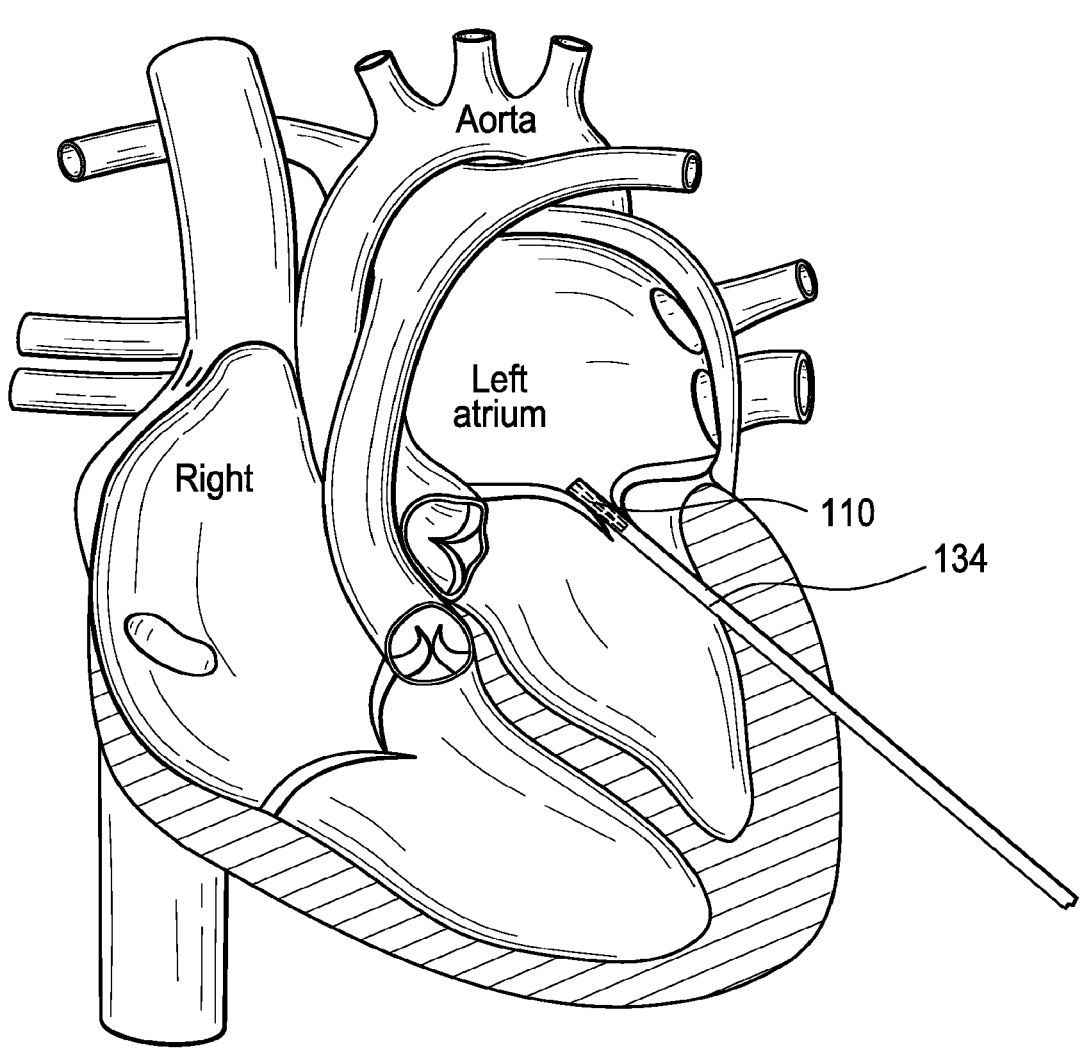
FIGS. 22 A-B is a pair of drawings of the lateral deployment of one embodiment of a prosthetic valve according to the present invention.
FIG. 22B is a detail view of an illustration of the prosthetic valve seated within the mitral annulus and tethered to the papillary muscles of the left ventricle.
Figure 22B:
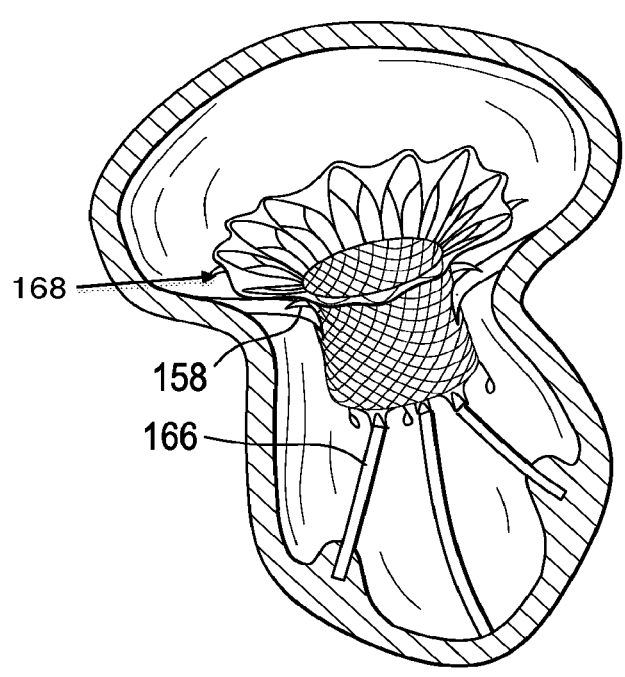

Referring now to FIGS. 22A-B, FIGS. 22A-B is a pair of drawings of the lateral deployment of one embodiment of a prosthetic valve according to the present invention and shows a prosthetic valve delivery catheter that has accessed the left atrium via the left ventricle by way of a lateral trans-ventricular wall approach through the lateral wall of the left ventricle of the heart. FIGS. 22A-B show a prosthetic valve delivery catheter that (A) has accessed the left atrium via the left ventricle by way of a lateral trans-ventricular wall approach through the lateral wall of the left ventricle of the heart, to be deposited the prosthetic valve into the left atrium, which will be withdrawn the delivery catheter for adjustment of the tethers, and (B) that has the valve adjusted and deployed within the mitral annulus.

FIG. 22B is an illustration of the prosthetic heart valve 110 seated within the mitral annulus and, in this embodiment, having papillary muscle tethers 166 within the left ventricle. FIG. 22B also shows annulus barbs 158, here shown optionally at both the transition point from the stent to the cuff 158 and elsewhere on the cuff itself 168.

Figure 23:
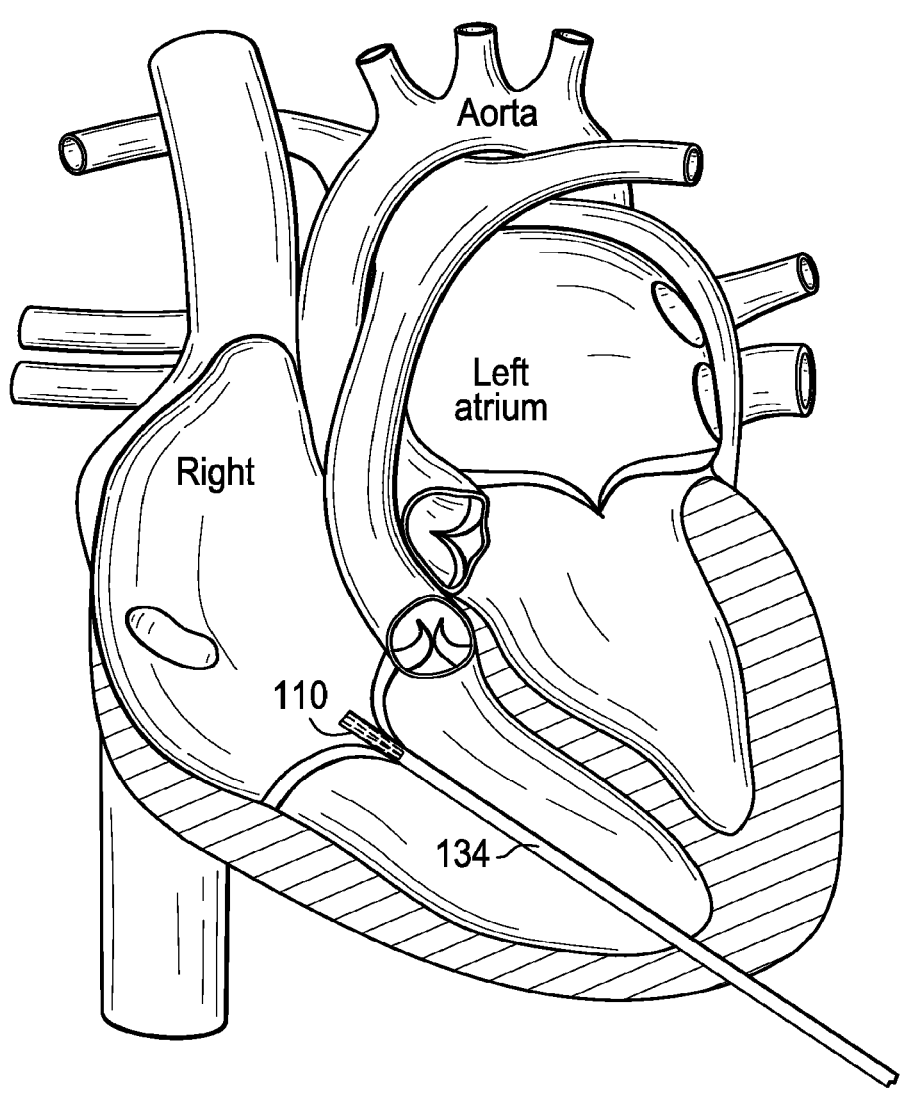
FIG. 23 is a cut-away view of a heart with a delivery catheter containing a prosthetic valve according to the present invention and accessing the right ventricle of the heart using an apical approach.

FIG. 23 is a cut-away view of a heart with a delivery catheter containing a prosthetic heart valve according to the present invention and accessing the right ventricle of the heart using an apical approach. FIG. 23 shows the delivery catheter advanced through to the tricuspid valve and into the right atrium for deployment of the prosthetic heart valve.

Figure 24A:
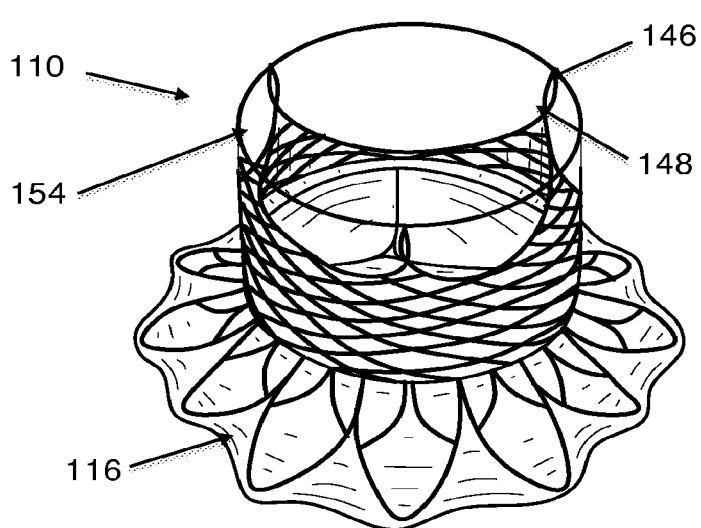
FIG. 24A is a bottom view from slightly above the horizontal plane of one embodiment of a prosthetic valve according to the present invention to show the bottom surface of the cuff and the halo feature.
Figure 24B:
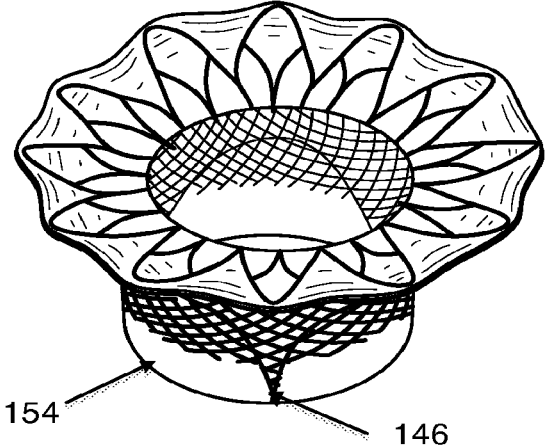
FIGS. 24 A-B shows an embodiment of a prosthetic valve having a ring or halo feature.

Referring now to FIGS. 24A-B that show an embodiment of a prosthetic valve 110 having a ring or halo feature 154. FIG. 24A is a bottom view from slightly above the horizontal plane of one embodiment of a prosthetic valve according to the present invention to show the bottom surface of the cuff 116 and the halo feature 154. FIG. 24B is a top view from slightly above the horizontal plane of one embodiment of a prosthetic valve according to the present invention to show the top surface of the cuff 116.

FIGS. 24A-B show an embodiment of a prosthetic valve having a ring or halo feature 154 attached to the junctions 146 of the arched wires 148 of leaflet assembly 118.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A prosthetic heart valve having a compressed delivery configuration and an expanded deployed configuration, the prosthetic heart valve comprising:

a self-expanding outer stent having a tubular body and an atrial cuff integral with and flaring away from the tubular body, a cuff covering being disposed on at least one of a distal-facing side and a proximal facing side of the atrial cuff;

a collapsible and expandable inner leaflet support member disposed within a lumen of the tubular body and attached to the outer stent so that the inner leaflet support member is positioned radially inward of the outer stent in both the compressed delivery configuration and in the expanded deployed configuration, the inner leaflet support member forming three commissural tips that extend beyond an outflow end of the outer stent;

a prosthetic leaflet structure attached to the inner leaflet support member such that the prosthetic leaflet structure is positioned radially inward of the outer stent in both the compressed delivery configuration and in the expanded deployed configuration; and an anchoring system including at least two wires extending from a ventricular end of the tubular body, the anchoring system not being directly attached to the prosthetic leaflet structure, wherein in the compressed delivery configuration of the prosthetic heart valve, the prosthetic heart valve is configured to be received within a delivery catheter so that the tubular body is positioned between the atrial cuff and the anchoring system, wherein, in a fully implanted condition of the prosthetic heart valve, the outer stent is shaped to contact inwardly facing surfaces of native leaflets of a native heart valve while the anchoring system anchors to a wall of a ventricle.

2. The prosthetic heart valve of claim 1, wherein the atrial cuff includes a plurality of radially extending loops collectively defining a collar shape and defining circumferential spaces between adjacent loops, the cuff covering being configured to permit the loops to articulate independently to conform to contours of an annulus of a native mitral or tricuspid valve.

3. The prosthetic heart valve of claim 2, wherein the loops have different lengths, defining an elongated collar.

4. The prosthetic heart valve of claim 2, wherein the cuff covering covers both the distal-facing side and the proximal-facing side of the atrial cuff and the radially outer ends of the loops.

5. The prosthetic heart valve of claim 2, wherein the cuff covering covers both the distal-facing side and the proximal-facing side of the atrial cuff and defines a peripheral edge of the atrial cuff that is spaced radially outwardly from the radially outer ends of the loops.

6. The prosthetic heart valve of claim 1, wherein the cuff covering is formed at least in part of a biocompatible synthetic material.

7. The prosthetic heart valve of claim 1, wherein the outer stent is formed of a nickel-titanium alloy.

8. The prosthetic heart valve of claim 7, wherein the inner leaflet support member is formed of a nickel-titanium alloy.

9. The prosthetic heart valve of claim 1, wherein the prosthetic heart valve is configured to replace a native mitral valve, and in the fully implanted condition of the prosthetic heart valve, the atrial cuff is configured to resist displacement of the prosthetic heart valve into the ventricle, the ventricle being a left ventricle.

10. The prosthetic heart valve of claim 9, wherein in the fully implanted condition of the prosthetic heart valve, the anchoring system is configured to resist displacement of the prosthetic heart valve into a left atrium.

11. The prosthetic heart valve of claim 1, wherein the atrial cuff covering is formed of cross-linked stabilized tissue, and the stabilized tissue is treated with anticoagulant.

12. The prosthetic heart valve of claim 1, wherein the cuff covering is formed of cross-linked stabilized tissue, and the stabilized tissue is heparinized.

13. The prosthetic heart valve of claim 1, wherein cuff covering is formed of cross-linked stabilized tissue, and the stabilized tissue has a thickness ranging from about 0.0762 mm and 0.254 mm.

14. The prosthetic heart valve of claim 1, wherein the prosthetic leaflet structure is formed of bovine pericardium.

15. The prosthetic heart valve of claim 1, wherein the atrial cuff forms an angle with respect to the tubular body in a range of between about 60 degrees and about 150 degrees when deployed.

16. The prosthetic heart valve of claim 1, wherein the three commissural tips can move independently of the outer stent.

17. The prosthetic heart valve of claim 16, wherein the three commissural are tips not directly coupled to the outer stent.

18. The prosthetic heart valve of claim 17, wherein the three commissural tips are capable of flexing inwardly or outwardly relative to the outer stent in the fully implanted condition of the prosthetic heart valve to relieve mechanical stresses on the prosthetic leaflet structure.

19. The prosthetic heart valve of claim 18, wherein the inner leaflet support member includes a portion which is directly coupled to the outer stent and which is spaced from the three commissural tips.

20. The prosthetic heart valve of claim 1, wherein the inner leaflet support member is a continuous and generally tubular wireform structure.

21. The prosthetic heart valve of claim 1, wherein the wall of the ventricle is a ventricular septum.

\*    \*    \*    \*    \*